(12) United States Patent
Zhou et al.

(10) Patent No.: US 11,478,433 B2
(45) Date of Patent: Oct. 25, 2022

(54) NANOMATERIALS WITH ENHANCED DRUG DELIVERY EFFICIENCY

(71) Applicant: Yale University, New Haven, CT (US)

(72) Inventors: Jiangbing Zhou, Cheshire, CT (US); Xin Yang, Harbin (CN); Chao Ma, Beijing (CN)

(73) Assignee: YALE UNIVERSITY, New Haven, CT (US)

( * ) Notice: Subject to any disclaimer, the term of this patent is extended or adjusted under 35 U.S.C. 154(b) by 36 days.

(21) Appl. No.: 16/624,803

(22) PCT Filed: Jun. 21, 2018

(86) PCT No.: PCT/US2018/038686
§ 371 (c)(1),
(2) Date: Dec. 19, 2019

(87) PCT Pub. No.: WO2018/237109
PCT Pub. Date: Dec. 27, 2018

(65) Prior Publication Data
US 2020/0214989 A1 Jul. 9, 2020

Related U.S. Application Data

(60) Provisional application No. 62/524,114, filed on Jun. 23, 2017.

(51) Int. Cl.
| | |
|---|---|
| *A61K 9/51* | (2006.01) |
| *A23L 33/10* | (2016.01) |
| *A61P 3/10* | (2006.01) |
| *A61P 35/04* | (2006.01) |
| *A61K 9/14* | (2006.01) |
| *A61K 31/56* | (2006.01) |
| *A61K 9/00* | (2006.01) |
| *B82Y 5/00* | (2011.01) |

(52) U.S. Cl.
CPC ............ *A61K 9/5123* (2013.01); *A23L 33/10* (2016.08); *A61K 9/145* (2013.01); *A61K 31/56* (2013.01); *A61P 3/10* (2018.01); *A61P 35/04* (2018.01); *A61K 9/0019* (2013.01); *A61K 9/0053* (2013.01); *B82Y 5/00* (2013.01)

(58) Field of Classification Search
CPC ....... A61K 9/5123; A61K 9/0053; A61P 3/10; B82Y 5/00
See application file for complete search history.

(56) References Cited

U.S. PATENT DOCUMENTS

| | | | |
|---|---|---|---|
| 5,019,400 A | 5/1991 | Gombotz | |
| 6,699,475 B1 | 3/2004 | Panicali | |
| 2008/0261916 A1* | 10/2008 | Jaszberenyi | ........... A21D 2/245 514/58 |
| 2017/0112800 A1* | 4/2017 | Roy | ................... A61K 39/3955 |

FOREIGN PATENT DOCUMENTS

| | | |
|---|---|---|
| CN | 106543037 | 3/2017 |
| WO | 2012078667 | 6/2012 |
| WO | 2013051994 | 4/2013 |
| WO | 2015077509 | 5/2015 |
| WO | 2016051013 | 4/2016 |
| WO | 2016185412 | 11/2016 |
| WO | 2016185413 | 11/2016 |
| WO | 2018237109 | 12/2018 |

OTHER PUBLICATIONS

Chairez-Ramirez, MH. et al. "Lupane-Type Triterpenes and Their Anti-Cancer Activities Against Most Common Malignant Tumors: A Review" Excli Journal 2016;15:758-771 (Year: 2016).*
OSU (https://lpi.oregonstate.edu/mic/dietary-factors/phytochemicals/phytosterols) 2005, pp. 1-29 (Year: 2005).*
Bildziukevich et al. "Spectral and microscopic study of self-assembly of novel cationic spermine amides of betulinic acid" Steroids 117 (2017) 90-96 (Year: 2017).*
Li et al. "pH-Sensitive mesoporous silica nanoparticles anticancer prodrugs for sustained release of ursolic acid and the enhanced anti-cancer efficacy for hepatocellular carcinoma cancer" European Journal of Pharmaceutical Sciences 96 (2017) 456-463 (Year: 2017).*
Agrawal, et al., "Is nanotechnology a boon for oral drug delivery", Drug Discov. Today, 19: 1530-1546 (2014).
Anand, et al., "Bioavailability of curcumin: Problems and Promises", Mol. Pharm., 4:807-818 (2007).
Balint, et al., "Artemisinin and its derivatives: an important new class of antimalarial agents", Pharmacology & Therapeutics, 90:261-265 (2001).
Beijnen, et al., "Bioanalysis, Pharmacokinetics, and Pharmacodynamics of the Novel Anticancer Drug Paclitaxel (Taxol)", Semin. Oncol., 21:53-62 (1994).
Blanco, et al., "Principles of nanoparticle design for overcoming biological barriers to drug delivery", Nature Biotechnology, 33:941-951 (2015).

(Continued)

*Primary Examiner* — Andrew S Rosenthal
(74) *Attorney, Agent, or Firm* — Pabst Patent Group LLP

(57) ABSTRACT

Supramolecular particle compositions based on medicinal natural products (MNPs), their synthetic analogs and derivatives, and methods to prepare and use them are provided. Five classes of MNPs and their derivatives including diterpene resin acid, phytosterol, lupane-type pentacyclic triterpene, oleanane-type pentacyclic triterpene, and lanostane-type triterpene form functional nano- or micro-structures that are stable to strong acidic environment and effectively penetrate the gastrointestinal tract. Therapeutic, prophylactic, or diagnostic agents that generally have poor intestinal permeability are converted to bioavailable forms when delivered with these supramolecular particles. Among many others, small compound chemotherapeutic agents and peptide therapeutics encapsulated therein have a much greater plasma concentration following oral administration, and effectively controls and treat symptoms associated with tumors or diabetes.

17 Claims, 6 Drawing Sheets

(56) References Cited

OTHER PUBLICATIONS

Chalasani, et al., "A Novel Vitamin B12-nanosphere Conjugate Carrier System for Peroral Delivery of Insulin", Journal of Controlled Release: Official Journal of the Controlled Release Society, 117:421-429 (2007).
Choi, et al., "Enhanced Paclitaxel Bioavailability After Oral Administration of Pegylated Paclitaxel Prodrug for Oral Delivery in Rats", Int. J. Pharm., 280:221-227 (2004).
Fallarero, et al., "(+)-Dehydroabietic Acid, an Abietane-type Diterpene, Inhibits Stpahylococcus aureus Biofilms in Vitro", Int. J. Mol. Sci., 14:12054-12072 (2013).
Fasinu, et al., "An Overview of the Evidence and Mechanisms of Herb-Drug Interactions", Frontiers in Pharmacology, 3:69 (2012).
Grabrucker, et al., "Nanoparticles as Blood-Brain Barrier Permeable CNS Targeted Drug Delivery Systems," Top Med. Chem., p. 1-19, DOI: 10.1007/7355_2013_22 (2013).
Han, et al., "Increased Nanoparticle Delivery to Brain Tumors by Autocatalytic priming for Improved Treatment and Imaging", ACS Nano, 10:4209-4218 (2016).
Hern, et al., "Resin acids, IX. Cationic Cyclization of Pimaric Acid derivatives. Partial Synthesis of (-)-Hibaene", Florida Department of Chemistry, 31:2257-2265 (1966).
Iyer, et al., "Oral-Insulin—A Review of Current Status", Obes. Met., 12(3):179-185 (2010).
Jager, et al., "Antigen-specific immunotherapy and cancer vaccines", Int. J. Cancer, 106:817-20 (2003).
Kennedy, et al., "A role for antibodies in tumor immunity", Int. Rev. Immunol., 22:141-72 (2003).
Kesarwani, et al., "Bioavailability Enhancers of Herbal Origin: An Overview", Asian Pac. J. Trop. Biomed. 3: 253-266 (2013).
Koliaki, et al., "Incretin-based Therapy: A Powerful and Promising Weapon in the Tratment of Type 2 Diabetes Mellitus", Diabetes Ther., 2:101-121 (2011).
Kuipers, et al., "Beyond intestinal soap—bile acids in metabolic control", Nat. Rev. Endocrinol., 10:488-498 (2014).
Kumari, et al., "Nanotechnology: A Tool to Enhance Therapeutic Values of Natural Plant Products", Trends in Medical Research, 7:34-42, (2012).
Manner, et al., "New derivatives of dehydroabietic acid target planktonic and biofilm bacteria in *Staphylococcus aureus* and effectively disrupt bacterial membrane integrity", Eur. J. of Med. Chem., 102:58-79 (2015).
Muheem, et al., "A Review on the Strategies for Oral Delivery of Proteins and Peptides and Their Clinical Perspectives", Saudi Pharmaceutical Journal, 24:413-428 (2016).
Nauck, et al., "Normalization of Fasting Hyperglycaemia by Exogenous Glucagon-Like Peptide 1 (7-36 Amide) in Type 2 (Non-Insulin-Dependent) Diabetic Patients", Diabetologia, 36:741-744 (1993).
Newman, et al., "Natural Products as Sources of New Drugs Over the 30 Years From 1981 to 2010", J. Nat. Prod., 75:311-335 (2012).
Obata, et al., "Evaluation of Skin damage Caused by Percutaneous Absorption enhancers Using Fractal Analysis", J. Pharm. Sci., 89(4):556-561 (2000).
Pridgen, et al., "Polymeric Nanoparticle Drug Delivery Technologies for Oral Delivery Applications", Expert opinion on drug delivery, 12:1459-1473 (2015).
Pridgen, et al., "Transepithelial Transport of Fc-targeted Nanoparticles by the Neonatal Fc Receptor for Oral Delivery", Sci. Transl. Med., 5:213ra167 (2013).
Ruoslahti, et al., "Specialization of tumour vasculature", Nat. Rev. Cancer, 2:83-90 (2002).
Scanlan, et al., "The cancer/testis genes: review, standardization, and commentary", Cancer Immun., 4:1 (2004).
Singla, et al., "Paclitaxel and Its Formulations", Int. J. Pharm., 235:179-192 (2002).
Stellaard, et al., "Simultaneous Determination of Cholic Acid and Chenodeoxycholic Acid Pool Sizes and Fractional Turnover Rates in Human Serum Using 13C-labeled Bile Acids", J. Lipid Res., 25:1313-1319 (1984).
Strohbehn, et al., "Imaging the Delivery of Brain-Penetrating PLGA Nanoparticles in the Brain Using Magnetic Resonance", Journal of Neuro-Oncology, 121(3):441-449 (2015).
Sucher, "Insights From Molecular Investigations of Traditional Chinese Herbal stroke Medicines: Implications for Neuroprotective Epilepsy Therapy", Epilepsy Behav., 8:350-362 (2006).
Tosi, et al., "Peptide-engineered polylactide-co-glycolide (PLGA) nanoparticles for brain delivery of drugs: in vivo experiments and proof of concept", SfN Neurosci. San Diego (USA) 1:84 (2010).
Ukiya, et al., "Cytotoxic Activities of Amino Acid-Conjugate Derivatives of abietane-Type Diterpenoids against Human cancer Cell Lines", Chemistry & Biodiversity, 10:1260-1268 (2013).
Wada, et al., "Antiulcer Activity of Dehydroabietic Acid Derivatives", Chem. Pharm. Bull., 33:1472-1487 (1985).
Wang, et al., "Synthesis and drug delivery of novel amphiphilic block copolymers containing hydrophobic dehydroabietic moiety", Journal of Materials Chemistry B, 1:2324-2332 (2013).
Zhou, et al., "Biodegradable poly (amine-co-ester) tgerpo9lymers for targeted gene delivery", Nat. Mater., 11:2-90 (2012).
International Search Report for corresponding PCT application PCT/US2018/038686 dated Oct. 12, 2018.
Bag, et al., "Self-assembly of Renewable Nano-sized Triterpenoids", Chem. Rec., 17:841-873 (2017).
Bag, et al., "Vesicular and Fibrillar Gels by Self-Assembly of Nanosized Oleanolic Acid", Asian Journal of Organic Chemistry, 1:150-154 (2012b). Supporting Information.
Bag, et al., "Vesicular and Fibrillar Gels by Self-Assembly of Nanosized Oleanolic Acid", Asian Journal of Organic Chemistry, 1:150-154 (2012b).
Bag, et al., "Self-assembly of a renewable nano-sized triterpenoid 18b-glycyrrhetinic acid", RSC advances, 2: 8623-8626 (2012a).
Bag, et al., "First self-assembly study of betulinic acid, a renewable nano-sized, 6-6-6-6-5 pentacyclic monohydroxy triterpenic acid", Nanoscale, 3: 4564-4566 (2011).
Chen, et al., "Oleanolic acid nanosuspensions: preparation, in-vitro characterization and enhanced hepatoprotective effect", Journal of pharmacy and pharmacology, 57: 259-264 (2005).
International Search Report for PCT/US2020/019925 dated May 26, 2020.
Patil, et al., "Novel self-assembled lithocholic acid nanoparticles for drug delivery in cancer", RSC advances, 3:19760-19764 (2013).

\* cited by examiner

NANOMATERIALS WITH ENHANCED DRUG DELIVERY EFFICIENCY

CROSS-REFERENCE TO RELATED APPLICATIONS

This application is a National Phase application under 35 U.S.C. 371 of PCT/US2018/038686, filed on Jun. 21, 2018, which claims the benefit of and priority to U.S. Application No. 62/524,114 filed Jun. 23, 2017, the contents of which are incorporated by reference in their entirety.

STATEMENT REGARDING FEDERALLY SPONSORED RESEARCH

This invention was made with government support under Grant No. NS095147 and Grant No. NS095817 awarded by the National Institutes of Health. The government has certain rights in the invention.

FIELD OF THE INVENTION

The invention relates generally to materials enhancing the delivery efficiency of drugs following oral administration and other routes of administrations.

BACKGROUND OF THE INVENTION

Drugs or therapeutics are taken into the body by one or more routes of administration. Common examples include oral and intravenous administration, while other routes can be utilized for local administration. Various factors such as solubility, stability, acidity, and irritancy of the drug, and the rate and the extent of absorption of the drug administered via different routes directly affect the therapeutic efficacy of delivered drugs.

For example, oral delivery is a highly sought-after means of drug administration due to its convenience and positive effect on patient compliance (Pridgen, E. M., et al., *Expert opinion on drug delivery*, 12:1459-1473 (2015)). However, oral drug delivery requires overcoming several physiological barriers. The highly acidic environment in the stomach (e.g., pH as low as 1.0) and the metabolic proteases may challenge the chemical stability and bioactivity of orally administered agents. The agents also need to cross the epithelial barrier of the intestinal mucosa for them to be transported from the lumen of the gut into the systemic circulation. Mucus can efficiently trap conventional particulate drug delivery systems via steric and/or adhesive interactions. The mucosal surface also undergoes a regular renewal/turnover process, resulting in poor retention and distribution of therapeutics before the epithelial surface. The epithelial cell layer includes tight junctions, limiting the penetration of molecules past the intestinal epithelium.

Approaches to transporting molecules from the gastrointestinal (GI) track into the systemic circulation include simple diffusion (paracellular and transcellular), carrier-mediated transport, active transport, and pinocytosis or endocytosis (Muheem A, et al., *Saudi Pharmaceutical Journal*, 24:413-428 (2016)). Chalasani and Pridgen have utilized receptor-mediated transcytosis pathways to improve the penetration of drugs by conjugation with ligands that target receptors in the intestinal epithelium, such as vitamin B 12 receptor (Chalasani, K. B., et al., *Journal of controlled release: official journal of the Controlled Release Society* 117, 421-429 (2007)) and neonatal Fc receptor (Pridgen, E. M. et al., *Sci Transl Med* 5, 213ra167 (2013)). But the complexity of chemical modifications to overcome GI track barriers and to achieve targeted drug delivery makes it difficult to translate into clinical applications.

Absorption enhancers or permeation enhancers such as fatty acids and bile salts have been studied to open up the tight junctions reversibly and improve the permeability of insulin and several other therapeutics. A common drawback of penetration enhancers for long-term usage is the potential damage or even dissolution of the biomembrane, leading to local inflammation (Obata Y, et al., *J. Pharm. Sci.*, 89(4): 556-561 (2000); Iyer H, et al., *Obes. Met.*, 12(3):179-185 (2010)). Large carriers for drug agents are unable to penetrate the gastrointestinal tract for efficient circulation in the blood stream (Blanco E, et al., *Nature biotechnology* 33, 941-951, (2015); Agrawal U, et al., *Drug Discov Today* 19, 1530-1546, (2014); Pridgen E M, et al., *Expert opinion on drug delivery* 12, 1459-1473, (2015)).

Although medicinal natural products (MNPs) accounted for more than half of the newly developed small molecule drugs over the period 1981-2010 (Newman, D. J. & Cragg, G. M., *J Nat Prod* 75, 311-335 (2012)), a major obstacle to MNP-based drug discovery is that over 90% of the isolated compounds cannot be used as drugs because of their poor stability, solubility, or pharmacokinetics. As such, chemical alterations or specific formulations of MNPs are often required for clinical applications (Kumari, A., et al., *Trends in Medical Research* 7, 34-42, (2012); Sucher, N J., Epilepsy Behav 8, 350-362, (2006)). Exemplary compounds include artemisinin (Balint G A, et al., *Pharmacology & therapeutics*, 90, 261-265 (2001)), paclitaxel (PTX, Singla A K, et al, *Int J Pharm*, 235, 179-192 (2002)), and curcumin (Anand P, et al., *Mol Pharm*, 4, 807-818 (2007)). Artemisinin, a compound purified from *Artemisia annua* L, has a bioavailability of less than 10% and is used mostly in its derivative forms (Balint, G. A., et al., *Pharmacology & therapeutics* 90, 261-265 (2001)). Paclitaxel, a compound purified from *Taxus* species, has poor solubility in aqueous solution and needs to be formulated, for example, with Cremophor EL for clinical applications (Singla, A. K., et al., Int J Pharm 235, 179-192 (2002)). Additionally, some MNPs such as *Poria cocos*, although commonly used in traditional medicine, do not contain pharmacologically active components. Some MNPs such as *Radix glycyrrhizae* and glycyrrhizin when co-administered may enhance the bioavailability of certain pharmaceutically active drugs, although these MNP extracts do not appear to contain active components (Kesarwani, K., et al., *Asian Pac J Trop Biomed* 3, 253-266 (2013); Fasinu, P. S., et al., *Frontiers in pharmacology* 3, 69 (2012)). The full potential of MNPs for oral delivery remains unclear as there is no fundamental understanding of the principles that govern complementary behaviors.

There remains a need to develop formulations for enhancing the delivery efficiency of orally delivered drugs, as well as for delivery via other routes of administration, especially for MNPs derived from plants, fungi, bacteria, or animals.

It is an object of the invention to provide compositions that can enhance delivery of agents to an individual in need thereof.

It is a further object of the present invention to provide compositions that protect pharmacologically active agents against the extreme acidic environment of the stomach and penetrate the intestine epithelium to enhance the bioavailability of the pharmacologically active agents following oral administration.

It is another object of the invention to provide methods to prepare and use these compositions for drug delivery.

SUMMARY OF THE INVENTION

Supramolecular nanoparticles based on isolated medicinal natural products (MNPs), their synthetic analogs and derivatives have been developed. Methods of making and using these supramolecular nanoparticles for delivery of therapeutic, prophylactic and/or diagnostic agents have also been developed. The MNPs enhance bioavailability following oral administration and/or improve targeting and therapeutic efficacy for other routes of administration. Selected MNP molecules and their synthetic analogs and derivatives (jointly referred to herein as MNPs unless otherwise stated) form supramolecular particles through noncovalent interactions (also termed functional nanomaterials or micromaterials), which upon oral delivery are efficiently transported from the gut to the blood stream, and upon other routes of delivery accumulate in diseased tissues such as tumors. The supramolecular particles can form based on hydrogen-bonding interactions, π-π interactions, solvophobic-solvophobic interactions, a combination thereof, or other non-covalent intermolecular interactions among the MNP-based compounds, their synthetic analogs and/or derivatives. In some embodiments, the structures of these molecules in formed supramolecular particles are planar or near planar with a stack or slipped-stack geometry. Any encapsulated drug agents in these supramolecular particles are efficiently transported and delivered. Alternatively, drug agents may be associated or bonded with these compounds; or they may be entrapped, non-covalently associated, or covalently bonded within, or on, the surface of, nanoparticles formed from these MNP-based compounds. Therefore, these isolated MNP-based compounds, their synthetic analogs or derivatives, in their supramolecular particle forms effectively convert compounds with low bioavailability (e.g., poor intestinal permeability) to an orally bioavailable form, and efficiently deliver drugs to diseases tissues via other routes of administration besides oral administration.

Compared with delivering unencapsulated, free form drug agents, the supramolecular particles exhibit a greatly improved efficiency in crossing the gastrointestinal (GI) tract and circulating in the blood stream for preferential accumulation at tumor sites of different tissues including the brain. Some embodiments provide that the selected MNP-based compounds and their synthetic analogs or derivatives are structurally defined such that they are transcytosized by the apical membrane of enterocytes as mediated by apical sodium-dependent bile transporter (ASBT) in the intestine. In preferred embodiments, these compounds are amphiphilic or hydrophobic small molecules having a molecular weight of less than 3,000, 2,000, 1,500, or 1,000 Da. Therefore, supramolecular particles formed from these MNP-based compounds and their synthetic analogs or derivatives provide greatly improved delivery and absorption of drug agents compared with common particulate carriers formed from polymers such as poly(lactic-co-glycolic acid). The strong acidity in the stomach does not damage these supramolecular particles, nor does it induce leakage of loaded drug agents from these supramolecular particles. These supramolecular particles generally show a similar release profile of encapsulated agents in different pHs, such as pH 7.4 and pH 1.0.

At least five classes of MNP-based compounds have been demonstrated to form supramolecular particles for effective delivery of different types of therapeutic, prophylactic, or diagnostic agents. These compounds are isolated from natural sources such as plants. Exemplary MNP-based compounds, from which synthetic analogs or derivatives are made and appreciated to function similarly, e.g., capable of forming supramolecular particles include diterpene resin acids (e.g., abietic acid and pimaric acid), phytosterols (e.g., stigmasterol and β-sitosterol), lupane-type pentacyclic triterpenes (e.g., lupeol and betulinic acid), oleanane-type pentacyclic tritepenes (e.g., glycyrrhetic acid and sumaresinolic acid), and lanostane-type triterpenes and derivatives (e.g., dehydrotrametenolic acid and poricoic acid A).

These compounds are isolated and extracted from natural plant, microbial, or animal products in one or more ways. In a first embodiment, a crude natural product is heated or boiled in water or an aqueous medium in the presence of one or more superparamagnetic metal oxide nanodots (e.g., superparamagnetic iron oxide (SPIO) nanodots), such that compounds capable of forming supramolecular nanoparticles are associated with the superparamagnetic metal nanodots, the complex of which is further isolated using a magnet. In a second embodiment, a plant, microbial, or animal product is immersed in an appropriate organic solvent such as dichloromethane, chloroform, and ethyl acetate, where the dissolved filtrate is collected (i.e., to remove undissolvable impurity and to enrich the compounds for forming supramolecular particles). The organic phase filtrate is emulsified in the presence of one or more superparamagnetic metal nanodots (e.g., SPIO nanodots), such that compounds to form supramolecular particles are associated with the superparamagnetic metal nanodots, forming a "complex" that is further isolated using a magnet. Using either approach, further purification of isolated compounds to separate from the SPIO nanodots usually involves immersing the compound-SPIO nanodots "complex" in an appropriate solvent to dissolve the compound and separate it from the SPIO nanodots by use of a magnet. Generally the superparamagnetic metal nanodots used in this process are coated with a surfactant molecule such as oleic acid to stabilize magnetic nanoparticles through a strong chemical bond between the functional group of the surfactant molecule (e.g., the carboxylic acid of the oleic acid) and the amorphous metal oxide nanoparticles.

The purified compounds from medicinal natural products, or their synthetic analogs and derivatives, are further processed into particulate forms (e.g., microparticles or nanoparticles) encapsulating a therapeutic, prophylactic, or diagnostic agent via emulsion or other techniques. In a preferred embodiment, these compounds form supramolecular nanoparticles via emulsion with a surfactant such as polyvinyl alcohol. In another embodiment, these compounds, generally amphiphilic or hydrophobic, form supramolecular nanoparticles via self-assembly in an aqueous environment.

The isolated and enriched MNP-based compounds, their synthetic analogs and derivatives, and supramolecular particles formed therefrom, provides improved safety besides enhanced drug delivery efficiency, compared with a crude mixture of natural plant/microbial/animal-based product and drug agents for consumption as practiced in some traditional medicines. They are also suitable for administration to a subject via different routes including intravenous administration and local injections.

A wide variety of agents can be encapsulated, associated, bonded, or otherwise carried by supramolecular particles formed via noncovalent association of these enriched MNP-based compounds, their synthetic analogs and derivatives for treatment of different diseases and disorders. The isolated MNP-based small molecule compounds, generally amphiphilic or hydrophobic, are more enriched and purified compared to their original form in MNP. For example, the purity of such compounds after isolation and enrichment from MNP increases to greater than 80%, 85%, 90%, 95%, 97%, 98%, or 99% by weight.

Exemplary therapeutic, prophylactic, or diagnostic agents suitable for application include, but are not limited to, small molecules, peptide, or proteins. Agents that generally have poor intestinal permeability are particularly suitable. Some embodiments provide extracted poricoic acid A (PAA) and dehydrotrametenolic acid (DTA) from *Poria cocos* form supramolecular nanoparticles. DTA supramolecular nanoparticles effectively deliver paclitaxel, glucagon-like peptide-1, and glyburide, following oral administration, to treat cancer, diabetes, and stroke, respectively. When these agents are administered as the free form via oral administration, little to no improvement is seen with the disease.

DETAILED DESCRIPTION OF THE INVENTION

I. Definitions

Figure 1:
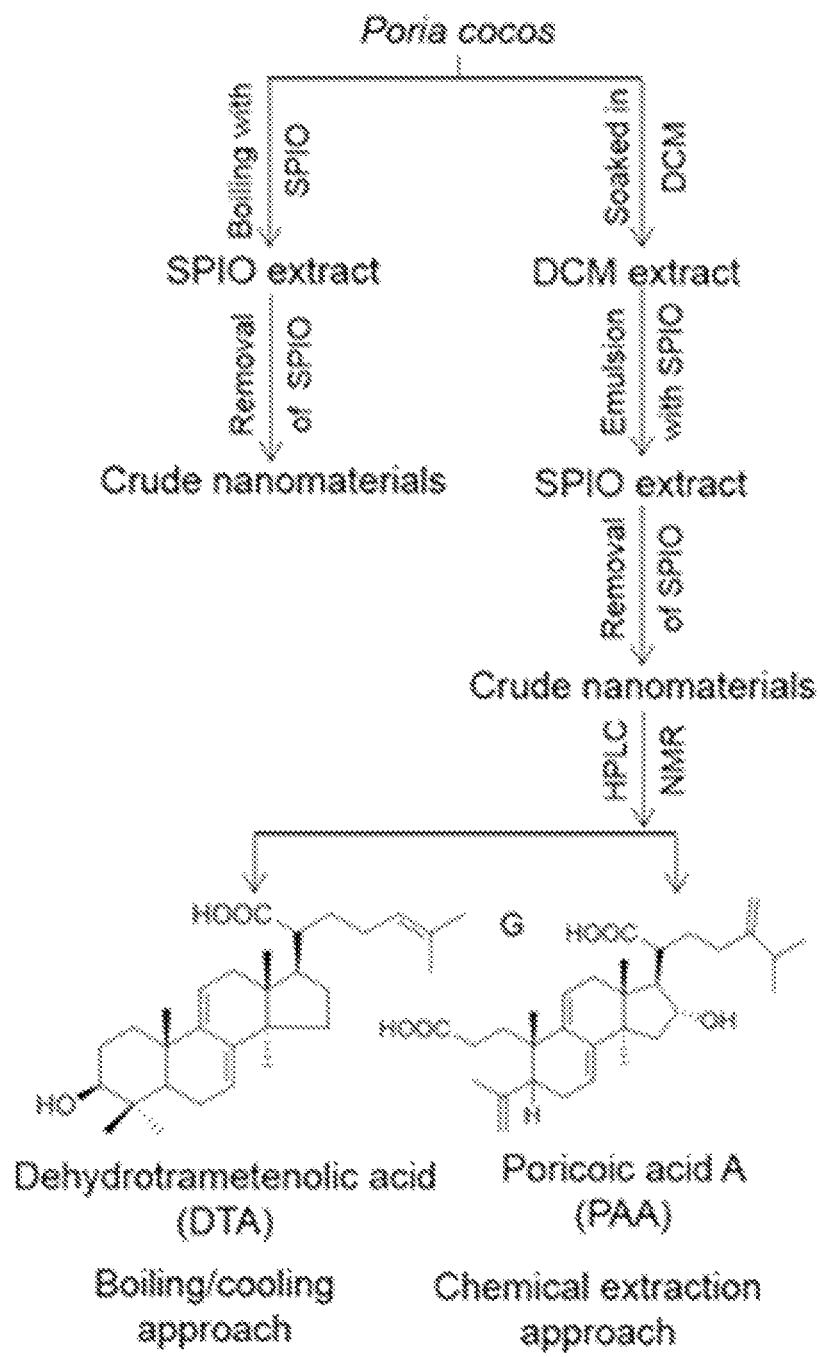
FIG. 1 is a diagram showing the processes of obtaining specific compounds capable of forming nanomaterials (e.g., sphere-shaped nanoparticles, rod-shaped nanoparticles) from an exemplary medicinal natural product, *Poria cocos*.

The term "medicinal natural product" refers to various classes of natural products from plant, microbial, and animal natural products, usually produced from sequences of metabolic activity, which have traditional or modern medicine values alone or in combination with other agents. Biosynthetic, semi-synthetic, or synthetic analogues or derivatives of medicinal natural product may share similar modes of action to medicinal natural product, which is intended to be encompassed by the present disclosure.

The term "nanoparticle" or "nanoparticulate" refers to a particle of any shape having a diameter from about 1 nm up to, but not including, about 1 micron. Nanoparticles having a spherical shape are generally referred to as "nanospheres". Nanoparticle or nanoparticulate compositions may have a spherical, hollow, and/or rod shape.

Microparticles may also be formed based on the identified compounds via common techniques to form microparticles. Microparticles generally refer to particles of any shape having a diameter from 1 μm up to a few millimeters. For penetration across GI track, nanoparticles formed from these identified compounds from medicinal natural products are preferred in some embodiment.

The term "supramolecular particle" refers to micro- or nano-particles formed from many molecules of one or more isolated compounds by noncovalent associations.

The term "bioavailability" refers to the proportion of a drug or other substance that enters the circulation when introduced into the body. It may be measured as a concentration of the delivered drug or substance in the plasma, or indirectly as the level of signal of the substrate that the delivered drug or substance acts on.

The term "oral formulation" refers to dosage units which may be administered to a patient by mouth. Exemplary oral formulations include tablets, capsules and pills.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically provided to the contrary, the term "substituted" refers to a structure, e.g., a chemical compound or a moiety on a larger chemical compound, regardless of how the structure was formed. The structure is not limited to a structure made by any specific method.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofurol[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —$CF_3$, —$CH_2$—$CF_3$, —$CCl_3$); —CN; —NCOCOCH$_2$CH$_2$; —NCOCOCHCH; —NCS; and combinations thereof.

The term "sulfonyl" is represented by the formula

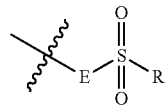

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$-R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "derivatives" in one or more relevant contexts include replacement of one or more hydrogen, methyl, carboxyl, hydroxyl, or $C_2$-$C_4$ alkyl or alkene with one or more of amine, carboxyl, amide, carbonyl, (straight or branched) $C_1$-$C_{20}$ alkyl, polyethylene glycol, aryl (including phenyl, indole), $C(=O)NR_1R_2$ (where $R_1$ denotes hydrogen, alkyl or aryl; and $R_2$ denotes heterocyclic unsaturated or saturated radical having 1 to 4 heteroatoms of elements nitrogen, oxygen, and/or sulfur from the group including furanyl, oxazolyl, isooxazolyl, thiophenyl, thiazolyl, isothiazolyl, pyrrolyl, imidazolyl, pyrazolyl, oxadiazolyl, thiadiazoyl, pyridyl, pyrimidinyl, pyrazinyl, pyridazinyl, triazinyl, triazolyl, tetrazolyl, it being possible for the heterocyclic radical to be substituted once or twice, identically or differently, by halogen, $C_1$~$C_2$-alkyl, $C_1$~$C_4$-alkoxy, $C_1$~$C_4$-alkylthio, hydroxy, mercapto, trifluoromethyl, nitro, phenyl, nitrile, carboxy or $C_1$~$C_4$-alkoxycarbonyl). One or more carbons referred to herein may be substituted or unsubstituted.

The term "treating" preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine;

The phrase "therapeutically effective amount" refers to an amount of the therapeutic agent that, when incorporated into and/or onto particles, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refers to incorporating, formulating, or otherwise including an active agent into and/or onto a composition that allows for release of such agent in the desired application. The terms contemplate any manner by which a therapeutic agent or other material is incorporated into a polymer matrix, including, for example, attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition. More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

II. Compositions

A. Medicinal Natural Product-Based Compounds, their Synthetic Analogs and Derivatives in the Form of Supramolecular Particles 1. Compounds Certain classes of MNPs, their synthetic analogs and derivatives, self-assemble or can be processed (e.g., emulsified) to form supramolecular particles to encapsulate, associate, incorporate, or otherwise carry different types of drugs (e.g., small compound and peptide). These supramolecular particles penetrate the gastrointestinal tract with high efficiency for oral delivery. They are also suitable for other routes of delivery for targeted accumulation at tumors and/or enhanced drug loading and delivery. For those drugs that are normally not suitable for oral delivery due to poor GI penetration, these supramolecular particles are able to convert them to orally available therapeutics by enhancing the penetration through the gastrointestinal tract into the circulation system. These supramolecular particles, particularly supramolecular nanoparticles, are in a spherical or rod shape, for efficient drug encapsulation. The penetration across the GI tract by the drug-carrying nanoparticulate MNPs is generally mediated by hijacking the apical sodium-dependent bile acid transporter (ASBT)-based intestinal transport system, which achieves oral delivery of small molecule and protein drugs for treatment of different diseases.

Exemplary classes of MNP-based compounds for supramolecular particles for delivering drugs include (i) diterpene compounds; (ii) phytosterols; (iii) lupane pentacyclic triterpenes; (iv) oleanane-type pentacyclic triterpenes; and (v) lanostane-type triterpenes; and compounds similar in structures to compounds in these classes, as well as their derivatives. The classification of compounds are not necessarily mutually exclusive. Compounds in one or two or more classes may be generalized to a broad chemical formula, where individual embodiments form supramolecular particles for enhancing delivery efficiency of drugs following administration.

Generally, compounds forming supramolecular particles have a general structure defined by formula 1.

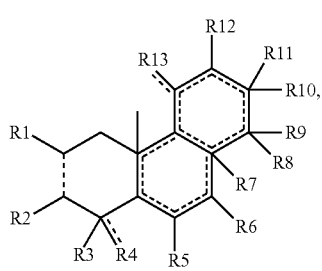

Formula 1 wherein R1 is H, OH, or C(=O)R16; R2 is H or R17; R3 is H, CH$_3$, or R18; R4, if single bonded, is H, CH$_3$ or R19, or R4, if double bonded, is CH$_2$; R5 is H or OH; R6 is H or OH; R7 is H or CH$_3$; R8 is H or CH$_3$; R9 is H or R14; R10 is R15 when R9 is R14, or R10 is R20 when R9 is H; R11 is H, CH$_3$, or R21; R12 is H or OH; R13, if single bonded, is H, or R13, if double bonded, is O or S; R14 and R15 combine to form a five-membered ring, a six-membered ring, or a six-membered ring fused with another five-membered or six-membered ring;

R16, R17, R18, R19, R20, or R21 are individually a derivatizing group comprising an amine, a polyethylene glycol, OH, a carboxyl, an alkyl, an alkene, an amide, a sulphonyl, an aryl, a carbohydrate, or a combination thereof;

wherein each dashed line between two atoms otherwise connected by a solid line indicates, individually, the two atoms are monovalently connected or divalently connected, the number of divalently connection not exceeding allowed valency in fused cyclic rings; and wherein the dash line between two atoms not otherwise connected by a solid line indicates a monovalent bond or no covalent bond.

In some embodiments where R1 is C(=O)R16; R2=R3=R5=R6=R7=R12=H; R13 is single bonded and is H; R4 is double bonded and is CH$_2$; R8=R11=CH$_3$; R9 is R14; R10 is R15; R14 and R15 combine to form a five-membered ring; the compounds are defined by formula 2:

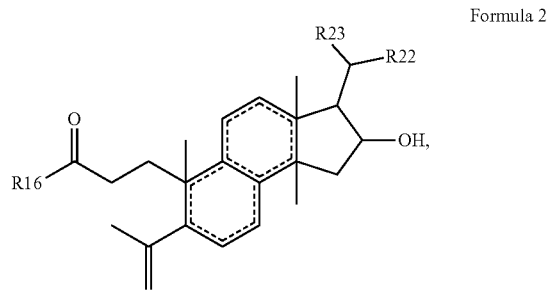

Formula 2 wherein R22 and R23 are individually a derivatizing group comprising a carboxyl, an alkyl, an alkene, a poly(ethylene glycol), an amine, OH, or a combination thereof.

Exemplary compounds having a structure defined by formula 2 include poricoic acid A, poricoic acid AE, derivatives thereof.

In another embodiment where R1=R5=R6=R7=R12=H; R2=OH or R17; R3 is H or CH$_3$; R4 is H or CH$_3$; R9 is R14; R10 is R15; R14 and R15 combine to form a five-membered ring; R11 is CH$_3$; R13 is single bonded and is H; the compounds are defined by Formula 3:

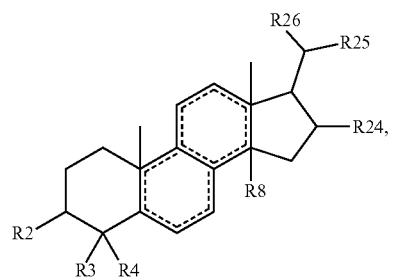

Formula 3 wherein R24 is H or OH; R25 and R26 are individually a derivatizing group comprising a carboxy, an alkyl, an alkene, a poly(ethylene glycol), an amine, OH, or a carboxyl with the hydrogen replaced by

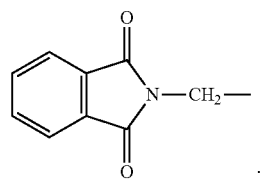

Exemplary compounds defined by formula 3 include dehydrotrametenolic acid, pachymic acid, beta sitosterol, cholesterol, ergosterol, campesterol, stigmasterol, and derivatives thereof.

In yet another embodiment where R1=R3=R4=R5=R7=R8=R13=H; R11 is CH$_3$; the compounds are defined by formula 4:

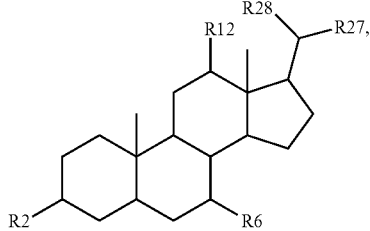

Formula 4 wherein R27 and R28 are individually a derivatizing group comprising a carboxyl, an alkyl, an alkene, a poly(ethylene glycol), an amine, an amide, OH, a sulphonyl.

Exemplary compounds defined by Formula 4 include cholic acid, glycocholic acid, taurocholic acid, deoxycholic acid, lithocholic, glycochenodeoxycholic acid, taurochenodeoxycholic acid, ursodeoxycholic acid, chenodeoxycholic acid, and derivatives thereof.

In yet another embodiment where R1=R2=R5=R6=R7=R8=R9=R12=R13=H; the compounds are defined by formula 5:

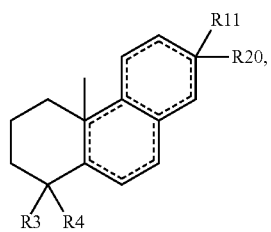

Formula 5 wherein R3, R4, R20 and R11 are individually a derivatizing group comprising a carboxyl, an alkyl, an alkene, a poly(ethylene glycol), an amine, an amide, a sulphonyl, OH, or a combination thereof.

Exemplary compounds defined by formula 5 include isopimaric acid, abietic acid, dihydroabietic acid, isodextropimaric acid, and derivatives thereof.

In yet another embodiment where R1 is H or OH; R4=R7=R8=CH$_3$; R6=R11=R12=H; R9 is R14; R10 is R15; R14 and R15 combine to form a six-membered ring fused with another five-membered ring; the compounds are defined by Formula 6:

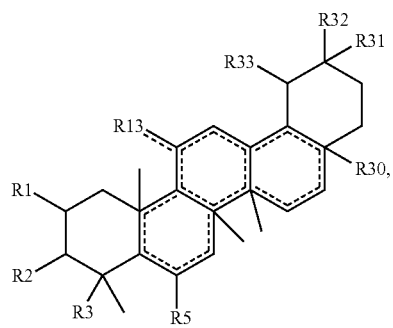

Formula 6 wherein R29 is H or OH; R30, R31, R32, and R33 are individually a derivatizing group comprising a carboxyl, an alkyl, an alkene, a poly(ethylene glycol), an amine, an amide, OH, a sulphonyl, or a combination thereof.

Exemplary compounds defined by Formula 6 are oleanolic acid, ursolic acid, sumaresinolic acid, echinocystic acid, maslinic acid, beta-boswellic acid, glycyrrhetic acid, glycyrrhizic acid, asiatic acid, and derivatives thereof such as these six:

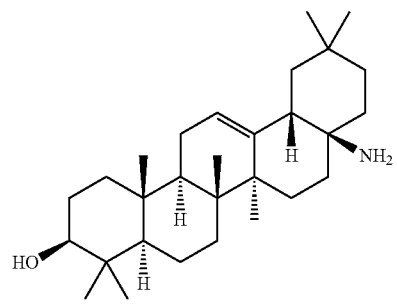

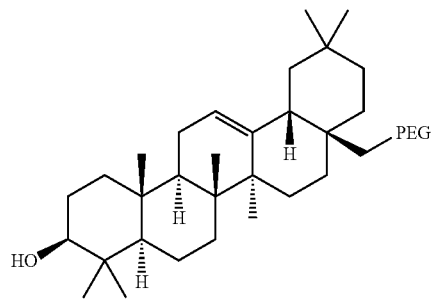

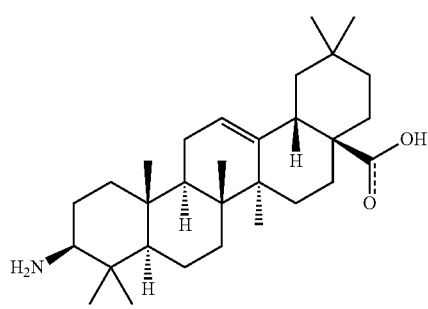

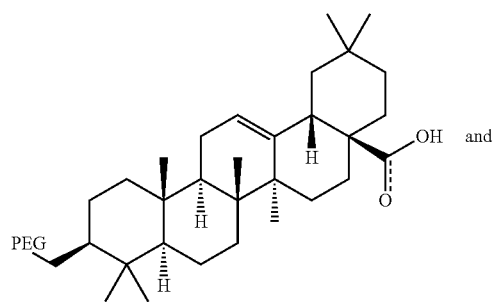

and

-continued

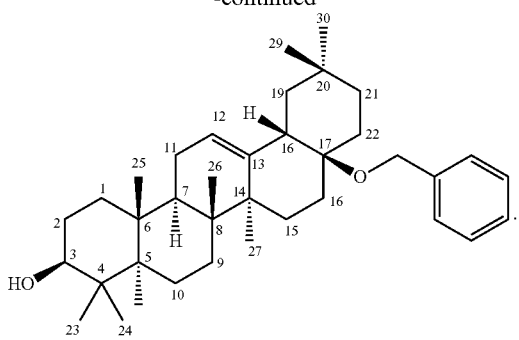

In yet another embodiment where R1=R5=R6=R11=R12=R13=H; R7=R8=CH$_3$; R9 is R14; R10 is R15; R14 and R15 combine to form a six-membered ring fused with another five-membered ring; the compounds defined by formula 7:

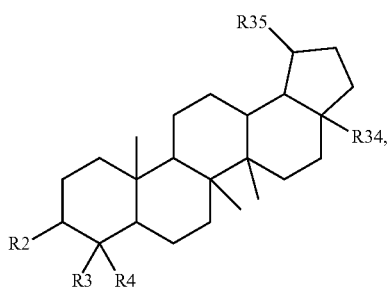

Formula 7 wherein R34 and R35 are individually a derivatizing group comprising a carboxyl, an alkyl, an alkene, a poly(ethylene glycol), an amine, an amide, OH, a sulphonyl, or a combination thereof.

Exemplary compounds defined by Formula 7 include lupeol, betulinic acid, betulin, and derivatives thereof.

These compounds can also be described in the following classes.

i. Diterpene-Class

Diterpene compounds contain two terpenes, which includes four isoprene units in linear or cyclic forms. Depending on the number of rings of in terpene compounds, there are compounds with no ring such as phytane; with 1 ring such as cembrene A; with 2 rings such as sclarene and labdane; with three rings such as abietane and taxadiene; and with 4 rings such as stemarene and stemodene. Although diterpene compounds may be isolated from botanical, microbial, and/or animal natural products, it is appreciated by one skilled in the art the synthetic variant and its derivatives will include similar properties to encapsulate drugs for high efficiency oral drug delivery based on the disclosure in this application.

Exemplary diterpene compounds include abietic acid, dehydroabietic acid, pimaric acid, isopimaric acid, and isodextropimaric acid with the following formulae.

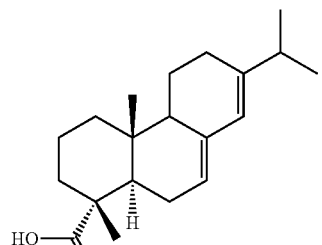
Abietic acid

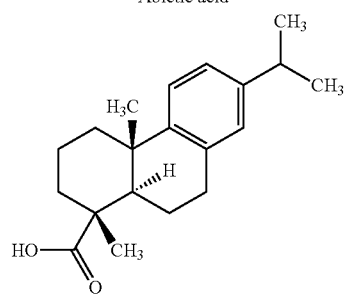
Dehydroabietic acid

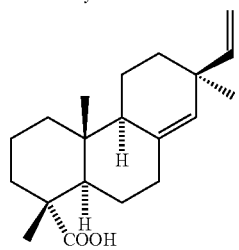
Pimaric acid

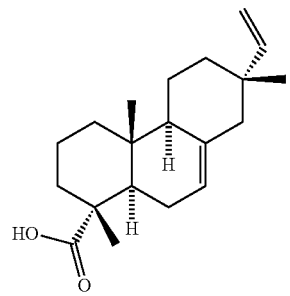
Isopimaric acid

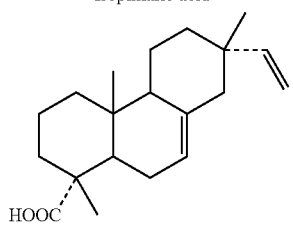
Isodextropimaric acid ii. Phytosterol-Class or Phytosterol-Like

Phytosterols are capable of forming supramolecular particles with heating and/or dissolution in appropriate solvent for encapsulation of drugs for oral delivery across the GI tract. Exemplary phytosterols include stigmasterol, ergosterol, beta sitosterol, cholesterol, campesterol with the following formula.

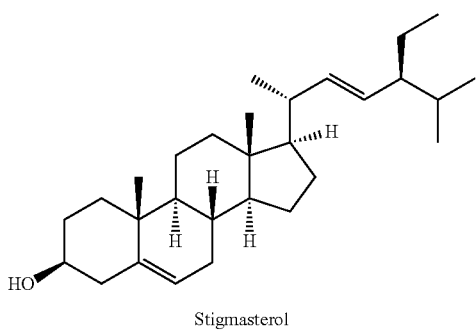
Stigmasterol

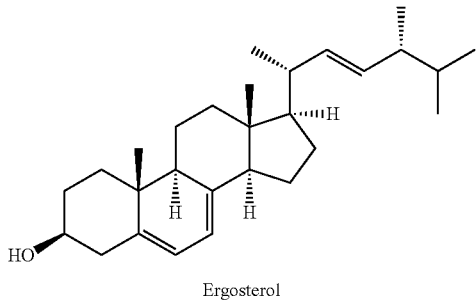
Ergosterol

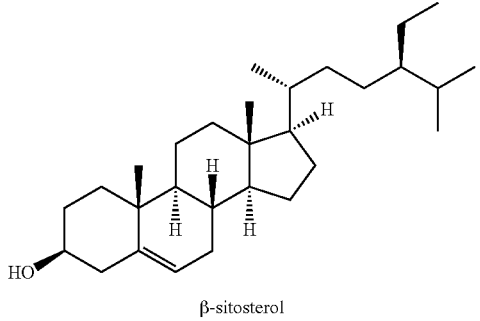
β-sitosterol

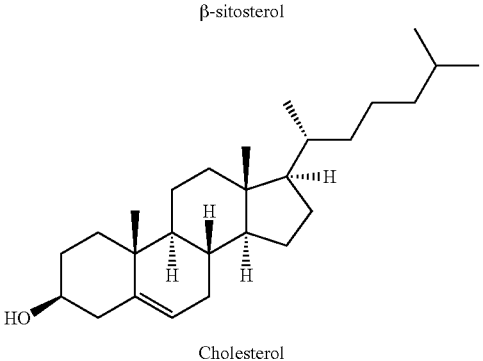
Cholesterol

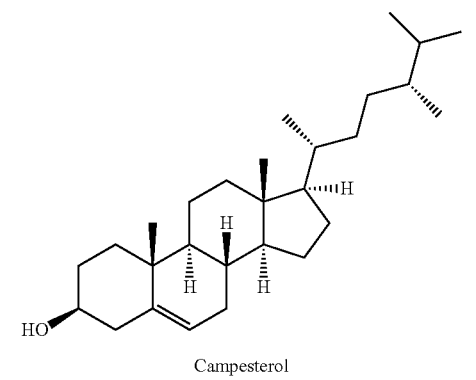
Campesterol

Although phytosterols may be isolated from botanical, microbial, and/or animal natural products, it is appreciated by one skilled in the art the synthetic variant and its derivatives will include similar properties to encapsulate drugs for high efficiency oral drug delivery based on the disclosure in this application.

iii. Lupane Pentacyclic Triterpenes

Lupane pentacyclic triterpenes are capable of forming nanoparticles with heating and/or dissolution in appropriate solvent for encapsulation of drugs for oral delivery across the GI tract. Exemplary lupane pentacyclic triterpene include lupeol, betulinic acid, and betulin with the following formulae.

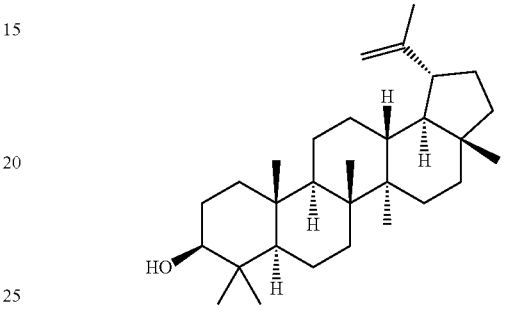
Lupeol

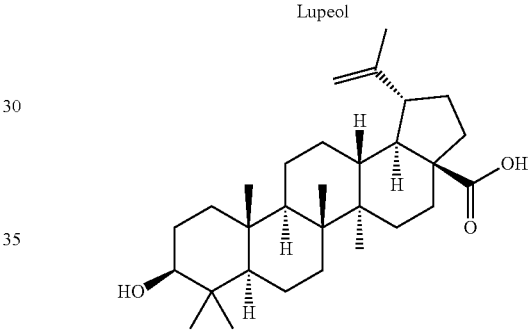
Betulinic acid

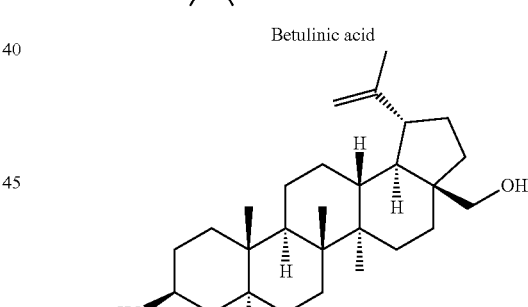
Betulin

Although pentacyclic triterpenes may be isolated from botanical, microbial, and/or animal natural products, it is appreciated by one skilled in the art the synthetic variant and its derivatives will include similar properties to encapsulate drugs for high efficiency oral drug delivery based on the disclosure in this application.

iv. Oleanane Type Triterpenes or Pentacyclic Triterpenoids

Pentacyclic triterpenes or pentacyclic triterpenoid-based compounds are capable of forming nanoparticles with heating and/or dissolution in appropriate solvent for encapsulation of drugs for oral delivery across the GI tract. Exemplary pentacyclic triterpene or triterpenoid-based compound include sumaresinolic acid, glycyrrhetic acid, oleanolic acid, ursolic acid, echinocystic acid, maslinic acid, D-boswellic acid, and glycyrrhizic acid with the following formulae.

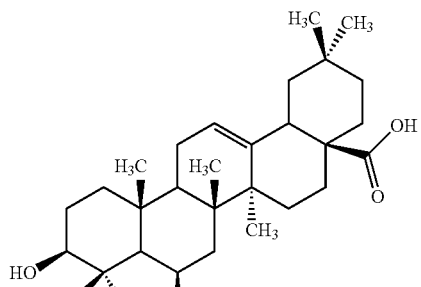

Sumaresinolic acid

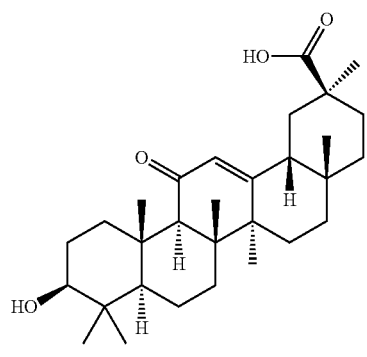

Glycyrrhetic acid

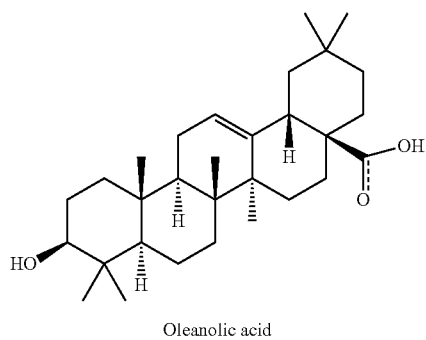

Oleanolic acid

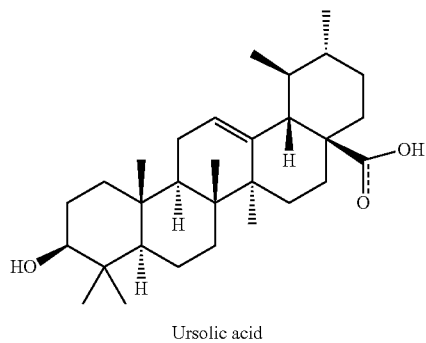

Ursolic acid

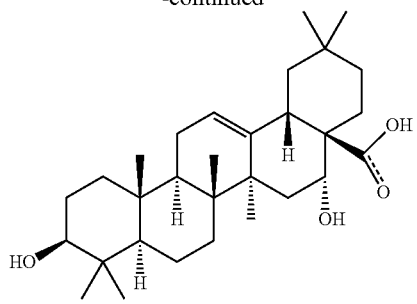

Echinocystic acid

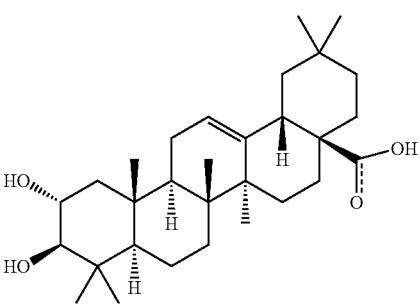

Maslinic acid

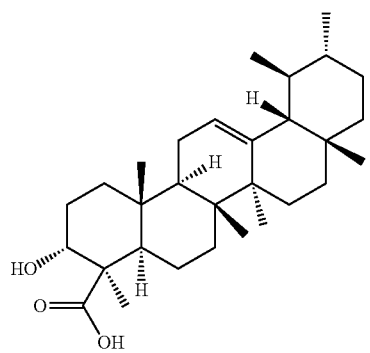

β-boswellic acid

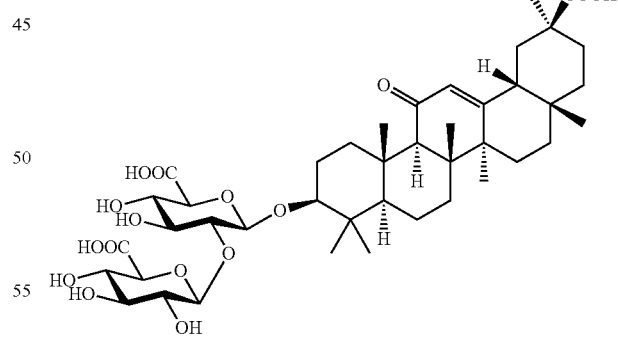

Glycyrrhizic acid v. Lanostane-Type Triterpenes and Derivatives

Triterpene compounds contain three terpenes, which includes six isoprene units in linear or cyclic forms. Tetracyclic triterpene-based compounds are capable of forming nanoparticles with heating and/or dissolution in appropriate solvent for encapsulation of drugs for oral delivery across the GI tract.

Exemplary tetracyclic triterpene compounds include dehydrotrametenolic acid, trametenolic acid, poricoic acid A, poricoic acid B, poricoic acid AE with the following formulae.

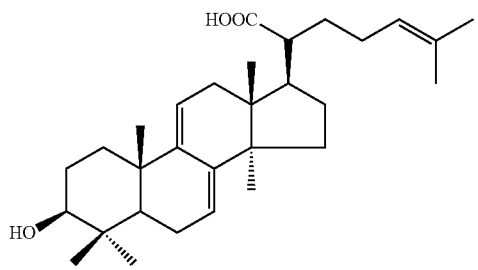

Dehydrotrametenolic acid (DTA)

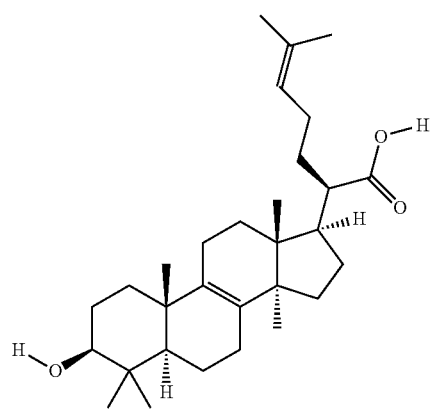

Trametenolic acid

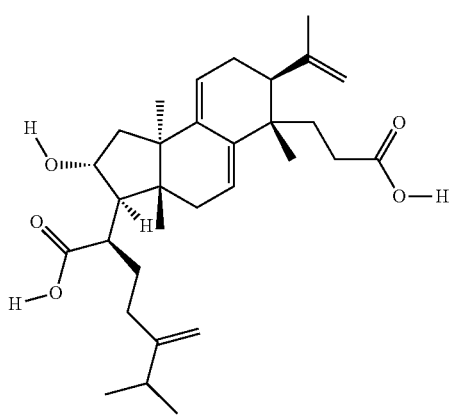

Poricoic acid A

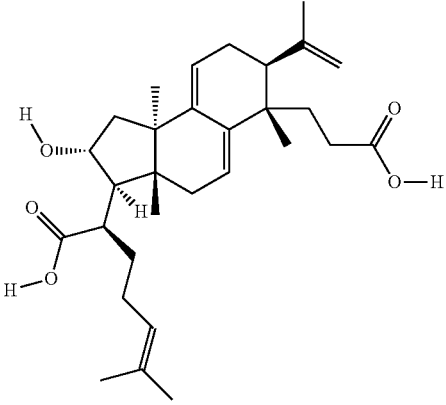

Poricoic acid B

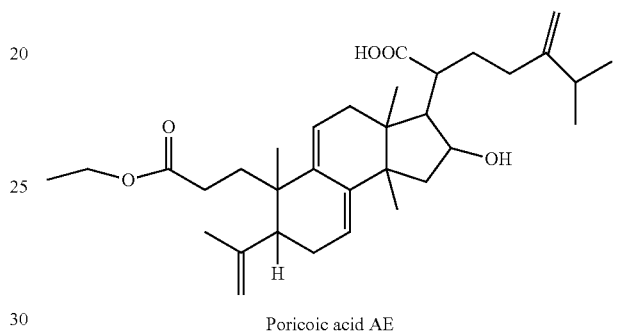

Poricoic acid AE

Tetracyclic triterpene derivatives capable of forming nanoparticulate morphology for encapsulation of drugs include those derived from substitution at one or more positions, e.g., by alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, or phosphonyl of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons. Although tetracyclic triterpene compounds may be isolated from botanical, microbial, and/or animal natural products, it is appreciated by one skilled in the art that synthetic variant and its derivatives will include similar properties to encapsulate drugs for high efficiency oral drug delivery.

2. Morphology and Properties of Formed Supramolecular Particles

MNPs-based compounds, their synthetic analogs or derivatives and drugs to be delivered are dissolved in appropriate solvent (e.g., organic solvent such as dichloromethane, chloroform, ethyl acetate) where these compounds form supramolecular particles via non-covalent interactions that encapsulate, associate, or otherwise incorporate drugs to be delivered. Inclusion of a surfactant may further improve the morphology of the formed supramolecular particles and reduce aggregation.

In one embodiment where boiling and cooling are used to extract/purify compounds from plants and other natural product, exemplary heating temperature includes about 40, 50, 60, 70, 80, 90, 100, and 110° C. Exemplary cooling temperature includes about 30, 25, 20, 15, 10, 5, and 0° C.

In some embodiments, the MNP-based compounds, their synthetic analogs or derivatives are emulsified in the presence of a surfactant to form supramolecular particles via non-covalent associations. Exemplary surfactants in forming supramolecular particles include anionic, cationic and non-ionic surfactants, such as, but not limited to, polyvinyl alcohol, F-127, lectin, fatty acids, phospholipids, polyoxyethylene sorbitan fatty acid derivatives, and castor oil. Other suitable surfactants include L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil, lecithin, oleic acid, and sorbitan trioleate.

Drug-containing supramolecular particles may be microparticles or nanoparticles of any shape. In some embodiments, supramolecular nanoparticles have a spherical or about spherical shape with an average diameter ranging from 10 nm and 700 nm, preferably between 50 nm and 500 nm, more preferably between 50 nm and 200 nm. They may also be in the form of nanorods with an average length ranging from 50 nm to 800 nm, preferably between 300 nm and 500 nm, with an average width between 5 nm and 180 nm, most preferably between 10 nm and 50 nm. Techniques to observe and measure nanostructures include scanning electron microscopy, transmission electron microscopy, atomic force microscopy, and/or dynamic light scattering. Particles of other geometries and sizes (e.g., microparticles) may be prepared from the MNP-based compounds. For oral delivery and GI track penetration mediated via apical sodium-dependent bile transporter, generally nano-sized formulations are preferred.

The supramolecular particles may encapsulate therapeutic agents that are hydrophilic or hydrophobic.

These nanoparticles generally have a negative surface charge, e.g., having zeta-potential at physiological environment between about 0 mV and −50 mV, or between −10 mV and −30 mV. They are generally acid stable, e.g., do not break or deform and excessively leak encapsulated drug in an acidic environment.

3. Solvent

Suitable organic solvents to extract and purify from medicinal natural products the one or more compounds capable of forming supramolecular particles include, but are not limited to, a polar or non-polar solvent, such as dichloromethane, DMSO, dipropylene glycol, propylene glycol, hexyl butyrate, glycerol, acetone, dimethylformamide (DMF), tetrahydrofuran, dioxane, acetonitrile, alcohol (e.g., ethanol, methanol or isopropyl alcohol, butyl alcohol, pentyl alcohol), benzene, toluene, carbon tetrachloride, acetonitrile, glycerol, 1,4-dioxane, dimethyl sulfoxide, ethylene glycol, chloroform, hexane, tetrahydrofuran, xylene, mesitylene, and/or any combination thereof. An organic solvent is generally selected based on the solubility of the crude and fine medicinal natural products therein, and may be affected by the polarity, hydrophobicity, water-miscibility, and in some cases the acidity of the solvent.

MNP-based compounds capable for encapsulation of drugs in a supramolecular particle form are typically purified from the extracts of different plant species such as *Poria cocos, Artenisia annua* L, *Taxus*, and *Radix Glycyrrhizae*. One or more approaches may be used to isolate and purify these compounds, including aqueous boiling and chemical (organic solvent) extraction methods with the help of super-paramagnetic nanoparticles. Purification method generally achieves about 100%, 95%, 90%, 85%, 80%, 75%, or 70% purity of the MNP compounds capable to form supramolecular particles, as measured by techniques such as high performance liquid chromatography or mass spectrometry.

Isolated compounds, especially via chemical extraction method, are generally purified to remove the organic solvent. Column chromatography, drying in vacuo, lyophilization, filtration, and centrifugation are exemplary techniques to separate the MNP-based compounds from solvents or impurities.

The amount of drug to be encapsulated in the supramolecular particles depends on the molecular weight, hydrophobicity/hydrophilicity, and polarity of the agent to be encapsulated and that of the supramolecular particle-forming compounds. Generally, drugs agents to be delivered are prepared with MNP-based compounds, their synthetic analogs or derivatives, at between about 1% and 80% by weight, preferably between about 5% and 70% by weight. Drug encapsulation efficiency may be about 100, 90, 85, 80, 70, 60, or 50%, with a drug loading efficiency in the formed nanoparticles of about 5, 7.5, 10, 15, 20, 30, 40, or 50%. Drug loading represents the weight content of drug in supramolecular particles. Drug encapsulation efficiency represents the ratio of final drug loading in comparison to the theoretical drug loading.

4. Optional Targeting Moieties

The supramolecular nanoparticles effectively cross the GI track and enter into the blood stream. They may migrate and accumulate to brain tissue. They preferentially accumulate at tumor sites, including those in the brain. Optionally, one or more targeting moieties (also referred to herein as targeting molecules, and targeting signals) can be loaded into, attached to the surface of, and/or enclosed within the supramolecular nanoparticles. In some embodiments, no targeting moieties are needed.

Exemplary target molecules include proteins, peptides, nucleic acids, lipids, saccharides, or polysaccharides that bind to one or more targets associated with an organ, tissue, cell, or extracellular matrix, or specific type of tumor or infected cell. Preferably, the targeting moiety is displayed on and preferably conjugated to the exterior surface of the supramolecular particles. Preferably, the targeting moiety increases or enhances targeting of the supramolecular particles to the brain. In some embodiments, the targeting moiety increases or enhances targeting of the supramolecular particles across the blood brain barrier (BBB), and/or to brain cells, preferably diseased or abnormal brain cells. In some embodiments, the targeting moiety increases or enhances targeting of the supramolecular particles to cells in the brain that are not brain cells. For example, the targeting moiety can increase targeting of the supramolecular particles to cancer cells that were not originally derived from a brain cell (e.g., brain metastases). Various techniques can be used to engineer the surface of supramolecular particles, such as covalent linkage of molecules (ligands) to nanosystems (polymers or lipids) (Tosi, et al., SfN Neurosci San Diego (USA), 1:84 (2010)).

The degree of specificity with which the supramolecular particles are targeted can be modulated through the selection of a targeting molecule with the appropriate affinity and specificity. For example, antibodies are very specific. These can be polyclonal, monoclonal, fragments, recombinant, or single chain, many of which are commercially available or readily obtained using standard techniques. T-cell specific molecules and antigens which are bound by antigen presenting cells as well as tumor targeting molecules can be bound to the surface of the supramolecular particles. The targeting molecules may be conjugated to the terminus of one or more PEG chains present on the surface of the particles.

In some embodiments, the targeting moiety is an antibody or antigen binding fragment thereof that specifically recognizes a tumor marker that is present exclusively or in elevated amounts on a malignant cell (e.g., a tumor antigen). Fragments are preferred since antibodies are very large, and can have limited diffusion through tissue. Suitable methods of conjugating targeting molecules that can be used to direct the supramolecular particles to cells and tissues of interest are known in the art. See, for example, Ruoslahti, et al. *Nat. Rev. Cancer*, 2:83-90 (2002).

Targeting molecules can also include neuropilins and endothelial targeting molecules, integrins, selectins, adhesion molecules, cytokines, and chemokines.

In some embodiments, the targeting moiety is an antibody or an antibody binding domain in combination with an antibody binding domain. The antibody can be polyclonal, monoclonal, linear, humanized, chimeric or a fragment thereof. The antibody can be antibody fragment such as Fab, Fab', F(ab'), Fv diabody, linear antibody, or single chain antibody. Antibody binding domains are known in the art and include, for example, proteins as Protein A and Protein G from *Staphylococcus aureus*. Other domains known to bind antibodies are known in the art and can be substituted.

Targeting molecules can be covalently bound to supramolecular particles using a variety of methods known in the art. In preferred embodiments the targeting moiety is attached to the supramolecular particles by PEGylation or a biotin-avidin bridge. The density of the targeting moiety can be important, depended on the affinity of a given moiety with cells or tissues of interest and stereospecific blockade. The density of moiety is preferably in the range of 20 to 1,000,000 per supramolecular particles, more preferable 50 to 10,000 per supramolecular particles; or having a surface density between 1 and 100 targeting molecules/100 nm$^2$ of surface area of the supramolecular particles.

i. Brain Targeting

In some embodiments, the targeting signal is directed to cells of the nervous system, including the brain and peripheral nervous system, or for the blood-brain barrier itself. Cells in the brain include several types and states and possess unique cell surface molecules specific for the type. Furthermore, cell types and states can be further characterized and grouped by the presentation of common cell surface molecules.

The targeting signal can be directed to specific neurotransmitter receptors expressed on the surface of cells of the nervous system. The distribution of neurotransmitter receptors is well known in the art and one so skilled in the art can direct the compositions using neurotransmitter receptor specific antibodies as targeting signals. Given the tropism of neurotransmitters for their receptors, in one embodiment the targeting signal consists of a neurotransmitter or ligand capable of specifically binding to a neurotransmitter receptor.

The targeting signal can be specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example, stem cells Exemplary markers specific for these cell types and states are well known in the art and include, but are not limited to, CD133 and Neurosphere.

Specific preferred brain targeting moieties are provided below in the working Examples, and include, but are not limited to, the peptide mHph2 and the peptide chlorotoxin (CTX).

The mode of transport of particles across the BBB is believed to be mediated by passive diffusion and/or receptor-mediated endocytosis, fluid phase endocytosis or phagocytosis, carrier-mediated transport or by absorptive-mediated transcytosis (Grabrucker, et al., "Nanoparticles as Blood-Brain Barrier Permeable CNS Targeted Drug Delivery Systems," *Top Med. Chem.*, pg. 1-19, DOI: 10.1007/7355_2013_22 (2013)). Passive diffusion can be enhanced by increasing the composition's plasma concentration, resulting in a larger gradient at the BBB and thus an increase in the amount of composition entering the CNS. One strategy for introducing supramolecular particles into the brain is receptor-mediated endocytosis. This strategy relies on the interaction of the particle surface ligand with a specific receptor in the BBB. Examples of suitable ligands include transferrin, transferrin receptor binding antibody, lactoferrin, melanotransferrin, folic acid, and a-mannose for NPs undergoing receptor-mediated transcytosis. (Grabrucker, et al., "Nanoparticles as Blood-Brain Barrier Permeable CNS Targeted Drug Delivery Systems," *Top Med. Chem.*, pg. 1-19, DOI: 10.1007/7355_2013_22 (2013)). It is believed that supramolecular particles engineered with such targeting moieties interact with the targeted receptor, create endocytotic vesicles, transcytosis across the BBB endothelial cells, and are subsequently exocytosed. Besides playing a role in nanoparticle uptake, surface engineering can be used to target different cell compartments. Because the vascular density in the brain is very high, once supramolecular particles have crossed the BBB, they will spread rapidly throughout the brain.

Therefore, in some embodiments, the targeting moiety targets, preferably by binding to, a BBB marker. Markers and even specific targeting moieties thereto, are known in the art and include, but are not limited to, transfer receptor (which can be targeted by, for example, OX26 antibody, and 8D3 antibody), insulin receptor (which can be target by, for example, 83-14 antibody or insulin), EGF receptor (which can be target by, for example, cetuximab and fragments (e.g., Fab') thereof), low-density lipoprotein receptor (which can be targeted by, for example, apolipoproteins such as ApoA, ApoE, etc.), thiamine receptor (which can be targeted with, for example, thiamine), transferrin receptor (which can be targeted with, for example, transferrin), folate receptor (which can be targeted with, for example, transferrin), glycoside receptor (which can be targeted with, for example, glycosides), lactoferrin receptor (which can be targeted with, for example, lactoferrin), insulin-like growth factor receptors (IGF1R & IGF2R) (which can be targeted with, for example, insulin like growth factor 1 & 2 (IGF-1 & IGF-2), and mannose-6-phosphate), leptin receptor (LEPR) (which can be targeted with, for example, leptin), Fc like growth factor receptor (FCGRT) (which can be target with, for example, IgG), scavenger receptor type B 1 (SCARB1) (which can be targeted with, for example, (modified lipoproteins, like acetylated low density lipoprotein (LDL)), and others targets and targeting moieties discussed in Alam, et al., *European Journal of Pharmaceutical Sciences*, 40:385-403 (2010), and Wong, et al., *Adv Drug Deliv Rev.*, 64(7): 686-700 (2012)).

In other embodiment, the markers are related to, or specific for, the condition being treated. For example, in some embodiments, the target moiety targets a marker of cancer (discussed in more detail below), stroke (e.g., MMP2, thrombin), epilepsy (e.g., MMP2), injury, or a neurological or neurodegenerative disease or disorder.

ii. Tumor-Specific and Tumor-Associated Antigens

In some embodiments, the targeting moiety is an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are known.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer,* 106:817-20 (2003); Kennedy, et al., *Int. Rev. Immunol.,* 22:141-72 (2003); Scanlan, et al. *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, so these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)), all of which can metastasize to the brain. Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci. USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession NO: U48722), HER2 (Yoshino, et al., *J. Immunol.,* 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and KO3193), vascular endothelial cell growth factor (GenBank NO: M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989); GenBank Acc. Nos. M65132 and M64928) NY-ESO-1 (GenBank Acc. Nos. AJ003149 and U87459), NA 17-A (PCT Publication NO: WO 96/40039), Melan-A/MART-1 (Kawakami, et al., *Proc. Nat. Acad. Sci. USA,* 91:3515 (1994); GenBank Acc. Nos. U06654 and U06452), tyrosinase (Topalian, et al., *Proc. Nat. Acad. Sci. USA,* 91:9461 (1994); GenBank Acc. NO: M26729; Weber, et al., *J. Clin. Invest,* 102:1258 (1998)), Gp-100 (Kawakami, et al., *Proc. Nat. Acad. Sci. USA,* 91:3515 (1994); GenBank Acc. NO: S73003, Adema, et al., *J. Biol. Chem.,* 269:20126 (1994)), MAGE (van den Bruggen, et al., *Science,* 254:1643 (1991)); GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. NO: U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, J. Exp. Med., 121:439 (1985); GenBank Acc. Nos. M59710, M59255 and M29540), and PyLT (GenBank Acc. Nos. J02289 and J02038); p97 (melanotransferrin) (Brown, et al., J. Immunol., 127:539-46 (1981); Rose, et al., Proc. Natl. Acad. Sci. USA, 83:1261-61 (1986)).

Additional tumor associated antigens include prostate surface antigen (PSA) (U.S. Pat. Nos. 6,677,157; 6,673,545); β-human chorionic gonadotropin β-HCG) (McManus, et al., Cancer Res., 36:3476-81 (1976); Yoshimura, et al., Cancer, 73:2745-52 (1994); Yamaguchi, et al., Br. J. Cancer, 60:382-84 (1989): Alfthan, et al., Cancer Res., 52:4628-33 (1992)); glycosyltransferase β-1,4-N-acetylgalactosaminyltransferases (GalNAc) (Hoon, et al., Int. J. Cancer, 43:857-62 (1989); Ando, et al., Int. J. Cancer, 40:12-17 (1987); Tsuchida, et al., J. Natl. Cancer, 78:45-54 (1987); Tsuchida, et al., J. Natl. Cancer, 78:55-60 (1987)); NUC18 (Lehmann, et al., Proc. Natl. Acad. Sci. USA, 86:9891-95 (1989); Lehmann, et al., Cancer Res., 47:841-45 (1987)); melanoma antigen gp75 (Vijayasardahi, et al., J. Exp. Med., 171:1375-80 (1990); GenBank Accession NO: X51455); human cytokeratin 8; high molecular weight melanoma antigen (Natali, et al., Cancer, 59:55-63 (1987); keratin 19 (Datta, et al., J. Clin. Oncol., 12:475-82 (1994)).

Tumor antigens of interest include antigens regarded in the art as "cancer/testis" (CT) antigens that are immunogenic in subjects having a malignant condition (Scanlan, et al., Cancer Immun., 4:1 (2004)). CT antigens include at least 19 different families of antigens that contain one or more members and that are capable of inducing an immune response, including, but not limited to, MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but are not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A 11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3, 4, 5, 6, 7, GnTV, Herv-K-mel, Lage-1, Mage-A1, 2, 3, 4, 6, 10, 12, Mage-$C_2$, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the disclosed fusion proteins.

iii. Antigens Associated with Tumor Neovasculature

Tumor-associated neovasculature provides a readily accessible route through which therapeutics can access the tumor. In one embodiment the viral proteins contain a domain that specifically binds to an antigen that is expressed by neovasculature associated with a tumor.

The antigen may be specific to tumor neovasculature or may be expressed at a higher level in tumor neovasculature when compared to normal vasculature. Exemplary antigens that are over-expressed by tumor-associated neovasculature as compared to normal vasculature include, but are not limited to, VEGF/KDR, Tie2, vascular cell adhesion molecule (VCAM), endoglin and $\alpha_5\beta_3$ integrin/vitronectin. Other antigens that are over-expressed by tumor-associated neovasculature as compared to normal vasculature are known to those of skill in the art and are suitable for targeting by the disclosed fusion proteins.

iv. Chemokines/Chemokine Receptors

In another embodiment, the supramolecular particles contain a targeting moiety that specifically binds to a chemokine, cytokine, or a receptor thereof. Chemokines are soluble, small molecular weight (8-14 kDa) proteins that bind to their cognate G-protein coupled receptors (GPCRs) to elicit a cellular response, usually directional migration or chemotaxis. Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are vital for tumor progression.

Based on the positioning of the conserved two N-terminal cysteine residues of the chemokines, they are classified into four groups: CXC, CC, CX3C and C chemokines. The CXC chemokines can be further classified into ELR+ and ELR– chemokines based on the presence or absence of the motif 'glu-leu-arg (ELR motif)' preceding the CXC sequence. The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

In some embodiments the targeting moiety targets (e.g., binds to) inflammation or a maker associated therewith, for example, an inflammatory cytokine, chemokine, or receptor thereof. Inflammatory chemokines are known in the art and include, but are not limited to, IL-1β, TNF-α, TGF-beta, IFN-γ, IL-17, IL-6, IL-23, IL-22, IL-21, and matrix metalloproteinases (MMPs).

B. Therapeutic, Prophylactic, Nutraceutical and/or Diagnostic Agents

The supramolecular particles may contain one or more suitable therapeutic, prophylactic, nutraceutical and/or diagnostic agents, jointly referred to herein as "drugs". Therapeutic, prophylactic and diagnostic agents may be proteins, peptides, sugars or polysaccharides, lipids or lipoproteins or lipopolysaccharides, nucleic acids (DNA, RNA, siRNA, miRNA, tRNA, piRNA, etc.) or analogs thereof, or small molecules (typically 2,000 D or less, more typically 1,000 D or less, organic, inorganic, natural or synthetic). The drug is selected based on the disease or disorder to be treated or prevented. In the preferred embodiment the drug is a chemotherapeutic or a protein or peptide such as glucagon-like peptide-1 (GLP-1). A wide range of drugs may be included in the compositions.

The active agents can be small molecule active agents or biomacromolecules, such as proteins, polypeptides, or nucleic acids. In some embodiments, the nucleic acid is an expression vector encoding a protein or a functional nucleic acid. Vectors can be suitable for integration into a cell genome or expressed extra-chromosomally. In other embodiments, the nucleic acid is a functional nucleic acid. Suitable small molecule active agents include organic and organometallic compounds. The small molecule active agents can be hydrophilic, hydrophobic, or amphiphilic compounds. The active agent can be a therapeutic, nutritional, diagnostic, or prophylactic agent.

Exemplary active agents include, but are not limited to, chemotherapeutic agents, neurological agents, tumor antigens, CD4+ T-cell epitopes, cytokines, imaging agents, radionuclides, small molecule signal transduction inhibitors, photothermal antennas, immunologic danger signaling molecules, other immunotherapeutics, enzymes, antibiotics, antivirals, anti-parasites, growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors, including, but not limited to, CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the nanoparticles into cells (including dendritic cells and other antigen-presenting cells), nutraceuticals such as vitamins, oligonucleotide drugs (including DNA, RNAs, antisense, aptamers, small interfering RNAs, ribozymes, external guide sequences for ribonuclease P, and triplex forming agents) and other gene modifying agents such as ribozymes, CRISPR/Cas, zinc finger nuclease, and transcription activator-like effector nucleases (TALEN).

Exemplary diagnostic agents include paramagnetic molecules, fluorescent compounds, magnetic molecules, and radionuclides, x-ray imaging agents, and contrast agents.

1. Chemotherapeutic Agents

In certain embodiments, the supramolecular particles include one or more anti-cancer agents. Exemplary chemotherapeutics for encapsulation in the supramolecular particles include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and *vinca* alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; anti-PD-1 (anti-programmed death-1) therapeutics such as antibodies or compounds (e.g., Nivolumab); thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

2. Neurological Agents

In some embodiment that active agent is a conventional treatment for stroke, or for increasing or enhancing neuroprotection. Exemplary neuroprotective agents are known in the art in include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin. Amantadine and anticholinergics are used for treating motor symptoms, clozapine for treating psychosis, cholinesterase inhibitors for treating dementia. Treatment strategies can also include administration of modafinil.

For subjects with Huntington's disease, dopamine blocker is used to help reduce abnormal behaviors and movements, and drugs such as amantadine and tetrabenazine are used to control movement, etc. Drugs that help to reduce chorea include neuroleptics and benzodiazepines. Compounds such as amantadine or ramacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

Treatments for Parkinson's disease, include, but are not limited to, levodopa (usually combined with a dopa decarboxylase inhibitor or COMT inhibitor), dopamine agonists, and MAO-B inhibitors.

The only compound yielding borderline significance with respect to survival time in subjects with ALS is riluzole (RILUTEK®) (2-amino-6-(trifluoromethoxy)benzothiazole), an antiexcitotoxin. Other medications, most used offlabel, and interventions can reduce symptoms due to ALS. Some treatments improve quality of life and a few appear to extend life. Common ALS-related therapies are reviewed in Gordon, *Aging and Disease,* 4(5):295-310 (2013), which is specifically incorporated by reference herein in its entirety. Exemplary ALS treatments and interventions are also discussed in Gordon, *Aging and Disease,* 4(5):295-310 (2013), listed in a table provided therein.

A number of other agents have been tested in one or more clinical trials with efficacies ranging from non-efficacious to promising. Exemplary agents are reviewed in Carlesi, et al., *Archives Italiennes de Biologie,* 149:151-167 (2011) and include, for example, agents that reduces excitotoxicity such as talampanel (8-methyl-7H-1,3-dioxolo(2,3)benzodiazepine), a cephalosporin such as ceftriaxone, or memantine; agents that reduce oxidative stress such as coenzyme Q10, manganoporphyrins, KNS-760704 [(6R)-4,5,6,7-tetrahydro-N6-propyl-2,6-benzothiazole-diamine dihydrochloride, RPPX], and edaravone (3-methyl-1-phenyl-2-pyrazolin-5-one, MCI-186); agents that reduces apoptosis such as histone deacetylase (HDAC) inhibitors including valproic acid, TCH346 (Dibenzo(b,f)oxepin-10-ylmethyl-methyl-prop-2-ynylamine), minocycline, or tauroursodeoxycholic Acid (TUDCA); agents that reduce neuroinflammation such as thalidomide and celastol; neurotropic agents such as insulin-like growth factor 1 (IGF-1) and vascular endothelial growth factor (VEGF); heat shock protein inducers such as arimoclomol; or an autophagy inducer such as rapamycin or lithium.

Exemplary neurological drugs include, but are not limited to, ABSTRAL® (fentanyl), AGGRENOX® (aspirin/extended-release dipyridamole), AMERGE® (naratriptan), AMPYRA® (dalfampridine), AMRIX® (cyclobenzaprine hydrochloride extended release), ANEXSIA®, APOKYN® (apomorphine hydrochloride), APTIOM® (eslicarbazepine acetate), ARICEPT® (donepezil hydrochloride), asprin, AVINZA® (morphine sulfate), AVONEX® (Interferon Beta 1-A), AXERT® (almotriptan malate), AXONA® (caprylidene), BANZEL® (rufinamide), BELSOMRA® (suvorexant), BOTOX® (onabotulinumtoxinA), BROMDAY® (bromfenac), BUTRANS® (buprenorphine), CAMBIA® (diclofenac potassium), CARBAGLU® (carglumic acid), CARBATROL® (Carbamazepine), CENESTIN® (synthetic conjugated estrogens, A), CIALIS® (tadalafil), KLONOPIN® (clonazepam), COMTAN® (Entacapone), COPAXONE® (glatiramer acetate), CUVPOSA® (glycopyrrolate), CYLERT®, DEPAKOTE® (divalproex sodium), DEPAKOTE® (divalproex sodium), DEPAKOTE ER® (divalproex sodium), DUOPA® (carbidopa and levodopa), DUREZOL® (difluprednate), DYLOJECT® (diclofenac sodium), EDLUAR® (zolpidem tartrate), ELIQUIS® (apixaban), EMBEDA® (morphine sulfate and naltrexone hydrochloride), EXALGO® (hydromorphone hydrochloride), EXELON® (rivastigmine tartrate), EXELON® (rivastigmine tartrate), EXPAREL® (bupivacaine liposome injectable suspension), EXTAVIA® (Interferon beta-1 b), FETZIMA® (levomilnacipran), FOCALIN® (dexmethylphenidate HCl), FROVA® (frovatriptan succinate), FYCOMPA® (perampanel), GALZIN® (zinc acetate), GRALISE® (gabapentin), HETLIOZ® (tasimelteon), HORIZANT® (gabapentin enacarbil), HORIZANT® (gabapentin enacarbil), IMITREX® (sumatriptan), IMITREX® (sumatriptan), INTERMEZZO® (zolpidem tartrate sublingual tablet), INTUNIV® (guanfacine extended-release), INVEGA® (paliperidone), NUMBY® (iontocaine), KADIAN® (Morphine Sulfate), KAPVAY® (clonidine hydrochloride), LEVETIRACTAM® (keppra), LAMICTAL® (lamotrigine), LAZANDA® (fentanyl citrate), LEMTRADA® (alemtuzumab), LEVITRA® (vardenafil), LUNESTA® (eszopiclone), LUPRON DEPOT® (leuprolide acetate), LUSEDRA® (fospropofol disodium), LYRICA® (pregabalin), MAXALT® (rizatriptan benzoate), MERREM I.V.® (meropenem), METADATE CD® (methylphenidate HCl), MIGRANAL® (dihydroergotamine), MIRAPEX® (pramipexole), MOVANTIK® (naloxegol), MYOBLOC® (rimabotulinumtoxinB), REVIA® (naltrexone hydrochloride), NAMENDA® (memantine HCl), NAMZARIC® (memantine hydrochloride extended-release+donepezil hydrochloride), NEUPRO® (Rotigotine Transdermal System), NEUPRO® (rotigotine), NEURONTIN® (gabapentin), NORCO® (Hydrocodone Bitartrate/Acetaminophen 10 mg/325 mg), NORTHERA® (droxidopa), NOVANTRONE® (mitoxantrone hydrochloride), NUCYNTA® (tapentadol), NUEDEXTA® (dextromethorphan hydrobromide and quinidine sulfate), NUVIGIL® (armodafinil), NYMALIZE® (nimodipine), ONFI® (clobazam), ONSOLIS® (fentanyl buccal), OXECTA® (oxycodone HCl), OXTELLAR XR® (oxcarbazepine extended release), OXYCONTIN® (oxycodone), PERCODAN® (oxycodone/aspirin), PERCOCET® (oxycodone with acetaminophen), PLEGRIDY® (peginterferon beta-1a), POSICOR® (mibefradil), POTIGA® (ezogabine), QUADRAMET® (samarium lexidronam), QUDEXY XR® (topiramate), QUILLIVANT XR® (methylphenidate hydrochloride), QUTENZA® (capsaicin), REBIF® (interferon beta-1a), REDUX® (dexfenfluramine hydrochloride), RELPAX® (eletriptan hydrobromide), REMINYL® (galantamine hydrobromide), REQUIP® (ropinirole hydrochloride), RILUTEK® (riluzole), ROZEREM® (ramelteon), RYTARY® (carbidopa and levodopa), SABRIL® (vigabatrin), ZELAPAR® (selegiline), SILENOR® (doxepin), SONATA® (zaleplon), SPRIX® (ketorolac tromethamine), STAVZOR® (valproic acid delayed release), STRATTERA® (atomoxetine HCl), SUBSYS® (fentanyl sublingual spray), TARGINIQ ER® (oxycodone hydrochloride+naloxone hydrochloride), TASMAR® (tolcapone), TEGRETOL® (carbamazepine), TIVORBEX® (indomethacin), TOPAMAX® (topiramate), TRILEPTAL® (oxcarbazepine), TROKENDI XR® (topiramate), TYSABRI® (natalizumab), ULTRACET® (acetaminophen and tramadol HCl), ULTRAJECT VERSED® (midazolam HCI), VIIBRYD® (vilazodone hydrochloride), VIMPAT® (lacosamide), VISIPAQUE® (iodixanol), VIVITROL® (naltrexone), VPRIV® (velaglucerase alfa), VYVANSE® (Lisdexamfetamine Dimesylate), XARTEMIS XR® (oxycodone hydrochloride and acetaminophen), XENAZINE® (tetrabenazine), XIFAXAN® (rifaximin), XYREM® (sodium oxybate), ZANAFLEX® (tizanidine hydrochloride), ZINGO® (lidocaine hydrochloride monohydrate), ZIPSOR® (diclofenac potassium), ZOHYDRO ER® (hydrocodone bitartrate), ZOMIG® (zolmitriptan), ZONEGRAN® (zonisamide), ZUBSOLV® (buprenorphine and naloxone).

3. Immune Modulators

The active agent can be an immunomodulator such as an immune response stimulating agent or an agent that blocks immunosuppression. In particularly preferred embodiments, the active agents target tumor checkpoint blockade or costimulatory molecules.

The immune system is composed of cellular (T-cell driven) and humoral (B-cell driven) elements. It is generally accepted that for cancer, triggering of a powerful cell-mediated immune response is more effective than activation of humoral immunity. Cell-based immunity depends upon the interaction and co-operation of a number of different immune cell types, including antigen-presenting cells (APC; of which dendritic cells are an important component), cytotoxic T cells, natural killer cells and T-helper cells. Therefore, the active agent can be an agent that increases a cell (T-cell driven) immune response, a humoral (B-cell driven) immune response, or a combination thereof. For example, in some embodiments, the agent enhances a T cell response, increases T cell activity, increases T cell proliferation, reduces a T cell inhibitory signal, enhances production of cytokines, stimulates T cell differentiation or effector function, promotes survival of T cells or any combination thereof.

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

In some embodiments the agent is an inflammatory molecule such as a cytokine, metalloprotease or other molecule including, but not limited to, IL-1β, TNF-α, TGF-beta, IFN-γ, IL-17, IL-6, IL-23, IL-22, IL-21, and MMPs.

a. Cytokines

In one embodiment, at least one of the active agents is a proinflammatory cytokine. Cytokines typically act as hormonal regulators or signaling molecules at nano- to-picomolar concentrations and help in cell signaling. The cytokine can be a protein, peptide, or glycoprotein. Exemplary cytokines include, but are not limited to, interleukins (e.g., IL-1, IL-2, IL-4, IL-5, IL-6, IL-7, IL-12, IL-15, etc.), interferons (e.g., interferon-γ), macrophage colony stimulating factor, granulocyte colony stimulating factor, tumor necrosis factor, Leukocyte Inhibitory Factor (LIF), chemokines, SDF-1α, and the CXC family of cytokines.

b. Chemokines

In another embodiment, at least one of the active agents is a proinflammatory chemokine. Chemokines are a family of small cytokines. Their name is derived from their ability to induce directed chemotaxis in nearby responsive cells. Therefore, they are chemotactic cytokines. Proteins are classified as chemokines according to shared structural characteristics such as small size (they are all approximately 8-10 kDa in size), and the presence of four cysteine residues in conserved locations that are key to forming their 3-dimensional shape. Chemokines have been classified into four main subfamilies: CXC, CC, CX3C and XC. Chemokines induce cell signaling by binding to G protein-linked transmembrane receptors (i.e., chemokine receptors).

4. Polynucleotides

The supramolecular particles can include a nucleic acid cargo. The polynucleotide can encode one or more proteins, can encode or be functional nucleic acids, or combinations thereof. The polynucleotide can be monocistronic or polycistronic. In some embodiments, the polynucleotide is multigenic. In some embodiments, the polynucleotide is transfected into the cell and remains extrachromosomal. In some embodiments, the polynucleotide is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the polynucleotide is incorporated into or part of a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, the polynucleotide of interest is operably linked to a promoter or other regulatory elements known in the art. Thus, the polynucleotide can be a vector such as an expression vector. The engineering of polynucleotides for expression in a prokaryotic or eukaryotic system may be performed by techniques generally known to those of skill in recombinant expression. An expression vector typically comprises one of the compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors. It will be appreciated that any of these vectors may be packaged and delivered using the disclosed polymers.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

5. Nutraceutical or Dietary Supplements

The supramolecular particles are also suitable for delivery of dietary supplements for oral consumption. These supplements and include vitamins, minerals, fiber, fatty acids, or amino acids, among other substances. Exemplary supplements to be delivered via MNP-based supramolecular nanoparticles include vitamins (e.g., vitamin A, B, C, D, E), essential amino acids, collagen, hydrolyzed collagen, calcium, glucosamine, chondroitin, lutein, and zeaxanthin.

C. Excipients

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

For oral delivery, the nanoparticulate MNPs encapsulating drugs may be further prepared using a pharmaceutically acceptable carrier composed of materials that are considered safe and effective and may be administered to an individual without causing undesirable biological side effects or unwanted interactions. The carrier is all components present in the pharmaceutical formulation other than the nanoparticulate MNPs encapsulating drugs.

The supramolecular particles may also be formulated as an inhalable dosage form as a powder or a solution. They are also suitable for injection, such as intravenous, intraperitoneal, or subcutaneous injection.

Suitable excipients are determined based on a number of factors, including the dosage form, desired release rate of the drug, stability of the drug to be delivered. Excipients include, but are not limited to, polyethylene glycols, humectants, vegetable oils, medium chain mono, di and triglycerides, lecithin, waxes, hydrogenated vegetable oils, colloidal silicon dioxide, polyvinylpyrrolidone (PVP) ("povidone"), celluloses, CARBOPOL® polymers (Lubrizol Advanced Materials, Inc.) (i.e. crosslinked acrylic acid-based polymers), acrylate polymers, other hydrogel forming polymers, plasticizers, crystallization inhibitors, bulk filling agents, solubilizers, bioavailability enhancers and combinations thereof.

For oral dosage forms for delivery to the intestinal mucosa, the drug-containing compositions may be in the form of tablets, mini-tab, multiparticulates (including micro- and nano-particles), osmotic delivery systems capsules, and liquids.

In some embodiment, the disclosed supramolecular particles encapsulating drugs are contained within a drug delivery device. A variety of different devices having a variety of different geometries and structures may be formed.

In another embodiment, the oral dosage form contains a matrix or a coating. A majority, but not all, of the surface of the matrix is coated with a protective or enteric coating. Optionally a portion of the surface of the matrix is coated with a bioadhesive layer.

Devices, matrices, or coatings for oral drug delivery may be formed using bioadhesive, biocompatible and/or biodegradable materials. In one embodiment, the devices are mixture of a Carbopol polymer, pectin and a modified cellulose, such as Carbopol 934 (BF Goodrich Co., Cleveland, Ohio), pectin (Sigma Chemicals, St. Louis, Mo.), and sodium carboxymethylcellulose (SCMC, Aldrich, Milwaukee, Wis.). Exemplary enteric coating materials include acrylate-based synthetic polymers such as Eudragit® (e.g., L- or S-series of Eudragit®) and natural materials such as shellac.

Optionally, the drug-containing supramolecular particles can be further encapsulated in a matrix or a capsule, such as a gelatin capsule. Optionally, the drug-containing supramolecular nanoparticles may be encapsulated in microparticles for controlled delivery.

III. Methods for Making MNP Nanoparticles and Screening One or More MNPs for a Drug Delivery Formulation

A. Isolation of MNP-Based Compounds Capable of Forming Nanoparticles.

Chemical Extraction Method

Dissolve a MNP source in an appropriate solvent, e.g. organic solvent such as dichloromethane, and subsequently emulsify with superparamagnetic metal oxide nanoparticles (e.g., nanodots), result in MNP-based compounds associated with the magnetic nanomaterials. Applying a magnetic force subsequently allows for isolation of MNP nanoparticles.

Dissolve in an appropriate solvent to separate supramolecular particles-forming MNP-based compounds from the magnetic nanomaterials. Subsequent workup includes washing away/diluting the surfactant, and removing the magnetic nanomaterials by applying a magnetic force.

Suitable superparamagnetic nanoparticles for isolation of compounds from the MNP source include superparamagnetic iron oxide (FeOx, e.g., $Fe_3O_4$) nanodots or nanocolloids, cobalt nanodots, semi-conducting metals such as Ga, Mn, As, Pt. One or more stabilizing agents or surfactants may coat the surface of these superparamagnetic nanoparticles including oleic acid or sodium oleate. Superparamagnetism (SPM) is a type of magnetism that occurs in small ferromagnetic or ferrimagnetic nanoparticles. This implies sizes around a few nanometers to a couple of tenth of nanometers, depending on the material. Additionally, these nanoparticles are single-domain particles.

Boiling/Soup Method

A MNP source can be boiled in water or aqueous environment for 30 minutes, one hour, two hours, three hours, or longer. After cooling to room temperature, the MNP can be collected by centrifugation and frozen and/or lyophilized for analysis of supramolecular particle structures under electron microscopy. After cooling, it can also be extracted via the chemical extraction method as described above.

B. Preparing Supramolecular Particles.

Some embodiments provide the MNP-based compounds, their synthetic analogs or derivatives self-assemble into supramolecular particles via non-covalent interactions. These supramolecular particles effectively penetrate the GI track. One or more therapeutic, prophylactic, or diagnostic agents are encapsulated or otherwise associated with the self-assembled particles, generally nanoparticles in the spherical shape or the rod shape.

Alternatively, the MNP-based compounds, their synthetic analogs or derivatives are processed into supramolecular particles to encapsulate or otherwise associate with or deliver one or more drug agents. Techniques for making particles include, but are not limited to, emulsion, solvent evaporation, solvent removal, spray drying, phase inversion, low temperature casting, and nanoprecipitation. Suitable methods of particle formulation are briefly described below. The therapeutic, prophylactic, or diagnostic agent and pharmaceutically acceptable excipients, including pH modifying agents, disintegrants, preservatives, and antioxidants, can optionally be incorporated into the particles during particle formation. As described above, one or more additional active agents can also be incorporated into the nanoparticle during particle formation.

1. Emulsion or Solvent Evaporation

In this method, the MNP-based compounds, their synthetic analogs or derivatives are dissolved in a volatile organic solvent, such as methylene chloride. The organic solution containing the MNP-based compounds, their synthetic analogs or derivatives is then suspended in an aqueous solution that contains a surface active agent such as poly (vinyl alcohol). The drug agents depending on the solubility may be dissolved in the organic solution or the aqueous solution. The resulting emulsion is stirred until most of the organic solvent evaporated, leaving solid nanoparticles. The resulting particles are washed with water and dried in a lyophilizer or in vacuo. Supramolecular particles with different sizes and morphologies can be obtained by this method.

Single emulsion (e.g., oil-in-water) and double emulsion (e.g., water-in-oil-in water) are both suitable for forming supramolecular particles.

2. Solvent Removal

In this method, the MNP-based compounds, their synthetic analogs or derivatives are dispersed or dissolved in a suitable solvent. This mixture is then suspended by stirring in an organic oil (such as silicon oil) to form an emulsion. Solid particles form from the emulsion, which can subsequently be isolated from the supernatant.

3. Spray Drying

In this method, the MNP-based compounds, their synthetic analogs or derivatives are dispersed or dissolved in a suitable solvent. The solution is pumped through a micronizing nozzle driven by a flow of compressed gas, and the resulting aerosol is suspended in a heated cyclone of air, allowing the solvent to evaporate from the microdroplets, forming particles.

4. Phase Inversion

In this method, the MNP-based compounds, their synthetic analogs or derivatives are dispersed or dissolved in a "good" solvent, and the solution is poured into a strong non solvent for the MNP-based compounds, their synthetic analogs or derivatives to spontaneously produce, under favorable conditions, nanoparticles.

5. Low Temperature Casting

Methods for very low temperature casting of nanoparticles are described in U.S. Pat. No. 5,019,400 to Gombotz et al. In this method, the MNP-based compounds, their synthetic analogs or derivatives are dispersed or dissolved is a solvent. The mixture is then atomized into a vessel containing a liquid non-solvent at a temperature below the freezing point of the solution which freezes the MNP-based compounds, their synthetic analogs or derivatives as tiny droplets. As the droplets and non-solvent for the components are warmed, the solvent in the droplets thaws and is extracted into the non-solvent, hardening the nanoparticles.

6. Nanoprecipitation

In this method, a solution containing one or more therapeutic, prophylactic, or diagnostic agents is added dropwise to a solution containing the MNP-based compounds, their synthetic analogs or derivatives. As the therapeutic, prophylactic, or diagnostic agents are complexed by the MNP-based compounds, their synthetic analogs or derivatives (e.g., through electrostatic charges), nanoparticles precipitate from solution. The resulting particles are isolated from solution, for example by filtration or centrifugation, washed, and dried using a lyophilizer.

In a particular embodiment, the supramolecular particles are prepared using an emulsification in method. In general, the particles are prepared by either o/w single emulsion or w/o/w double emulsion method as described in R. C. Mundargi et al, *J. Control. Release* 125, 193 (2008), M. Li et al., *Int. J. Pharm.* 363, 26 (2008), C. E. Astete and C. M. Sabliov, *J. Biomater. Sci. Polymer Ed.* 17, 247 (2006), and R. A. Jain, *Biomaterials*, 21, 2475 (2000). In this procedure, the polymer is dissolved in an organic solvent, such as dichloromethane, to form an oil phase. The oil phase is added to an aqueous solution of the emulsifier, typically under probe sonication for a period of time (e.g., 2 minutes) to form an emulsion. The emulsion is added to another large volume of the emulsifier with magnetic stirring to evaporate the organic solvent.

Nanoparticles are collected by centrifugation (e.g., 20,000 g for 25 mins) after filtering through a 1 μm size membrane filter and thoroughly washed with water. To prepare the nanoparticles for fluorescence microscopy or infrared imaging, a certain amount of ALEXA FLUOR® dyes or rhodamine B is blended in the emulsification process. After the complete removal of organic solvent, nanoparticles were collected by the same procedure as described above.

The diameter (nm), polydispersity index (PDI) and surface charge ((potential, mV) of nanoparticles can be measured by dynamic light scattering on Zetasizer Nano ZS90 (Malvern Instruments, Southborough, Mass.). The morphology of the nanoparticles can be characterized by transmission electron microscopy (TEM) or scanning electron microscopy (SEM).

IV. Methods of Use

The supramolecular particle compositions may be orally delivered to provide uptake through the gastrointestinal tract. The particle composition may also be delivered by intravenous, epidural, intracerebral, intracerebroventricular, topical, nasal, intraarticular, intracardiac, intracavernous, intradermal, intramuscular, intraocular, intraperitoneal, intrathecal, intravaginal, intravesical, intravitreal, subcutaneous, transdermal, or transmucosal administration.

In one preferred embodiment, the compositions are designed for drug delivery to the intestinal epithelium or across the intestinal epithelium. Transport takes place via one or more mechanisms including transcellular transport and paracellular transport. In one preferred embodiment, apical sodium dependent bile acid transporter facilitates the transport of drug-containing supramolecular particles.

The supramolecular particle compositions can be used to deliver small compound, peptide and protein medicines, such as those for the treatment of diabetes, hemophilia, inflammatory disease and disorders, nerve-related disorders, and tumors via one or more routes of administration.

Application may be through oral consumption, inhalation, systemic infusion, injection, transplantation, or topical application including to the mucosa, oral, buccal, nasal, intestinal, vaginal, rectal and skin.

The supramolecular particles in the circulation may preferentially accumulate in tumor. In some embodiments, they naturally penetrate to the brain, particularly at brain locations with injuries such as tumors, stroke, trauma, or neurological disease such as Alzheimer's disease. In some embodiments, the supramolecular particles and methods are used to treat cancer, particularly brain cancer; to treat neurodegenerative disorder, in need of neuroprotection, or a combination thereof; or to treat diabetes.

EXAMPLES

Example 1. Identification and Isolation of Nanomaterials from *Poria cocos*

Materials and Methods
Aqueous Boiling Method
*Poria cocos* is a saprophytic fungus often used in about 10% of the traditional Chinese medical preparations (Pharmacopoeia of People's Republic of China (Part I), B. C. M. S. P. (2010)). *Poria cocos* powder was boiled in water for one hour. After cooling to room temperature, the supernatant was collected by centrifugation and lyophilized. The supernatant was analyzed under transmission electron microscopy (TEM), and the lyophilized powder was analyzed by scanning electron microscope (SEM).

Aqueous Boiling in the Presence of SPIO Nanodots
To isolate supramolecular nanoparticles capable of drug encapsulation, *Poria cocos* powder was boiled in water with hydrophilic, oleic acid-coated superparamagnetic iron oxide (SPIO) nanodots having a diameter of 5-8 nm (Strohbehn, G. et al. *Journal of neuro-oncology* 121(3), 441-449 (2015)). These SIPO nanodots acted as a model cargo to facilitate the isolation of supramolecular nanoparticles formed from components in *Poria cocos*. After cooling down to room temperature, supramolecular nanoparticles encapsulating SPIO nanodots were collected using a magnet. Encapsulation of SPIO nanodots in supramolecular nanoparticles was confirmed by TEM.

After lyophilization, the SPIO nanodots-encapsulated supramolecular nanoparticles were dissolved in dichloromethane (DCM). Free SPIO nanodots were removed by magnetization. Following evaporation of DCM, supramolecular nanomaterials were obtained and resuspended in water for SEM analysis.

Chemical Extraction Method
To simplify the process, a chemical extraction approach without the need for heating was employed. *Poria cocos* powder was first soaked in DCM for 2 days. Filtration yielded DCM extract and removed undissolved crude mass. Next, the DCM extract was emulsified with SPIO nanodots. SPIO-encapsulated supramolecular nanoparticles were collected using magnetic force and analyzed under TEM. In some embodiments, polyvinyl alcohol was used as the emulsifer.

Subsequently to purify nanoparticles by removing SPIO nanodots, SPIO-encapsulated nanoparticles were dissolved in DCM and SPIO was removed using a magnet. The remaining materials after SPIO was removed were further separated using high performance liquid chromatography (HPLC) and analyzed via H-NMR and C-NMR.

Synthesis of Supramolecular Nanoparticles
The identified compounds as extracted from medicinal natural products and further collected via SPIO nanodots and magnetic force were prepared into supramolecular nanoparticles using standard emulsion procedures (Han L, et al., *ACS nano*, 10, 4209-4218 (2016); Zhou J, et al., *Nat Mater*, 11, 82-90 (2012)). For preparation of SNPs encapsulating hydrophobic cargos including SPIO, rhodamine B, IR780, and paclitaxel, the selected cargo was dissolved with the identified compounds in DCM, and added dropwise to a solution of 4 mL 5% PVA (aqueous phase). The resulting emulsion was sonicated on ice and added to a stirring solution of 0.3% PVA in water (aqueous phase). After evaporation at a selected temperature overnight, SNPs were collected by centrifugation, washed, and lyophilized for storage.

Scanning Electron Microscopy (SEM)
The morphology and size of nanoparticles were characterized using SEM and ImageJ, respectively. Samples were mounted on carbon tape and sputter-coated with gold, under vacuum, in an argon atmosphere, using a sputter current of 40 mA (Dynavac Mini Coater, Dynavac, USA). SEM imaging was carried out with a Philips XL30 SEM using a LaB electron gun with an accelerating voltage of 3 kV. The mean diameter and size distribution of the particles were determined by image analysis using image analysis software (ImageJ, National Institutes of Health). These micrographs were also used to assess particle morphology.

Dynamic Light Scattering (DLS)

The hydrodynamic diameter of nanoparticles was measured using dynamic light scattering. A transparent cuvette was filled nanoparticles in HPLC-grade water. The capped cuvette was placed in a Zetasizer (Malvern), and dynamic light scattering data or zeta potential was read.

Transmission Electron Microscopy (TEM)

Nanoparticle suspension was applied to holey carbon-coated copper grids (SPI, West Chester, Pa., USA) and imaged using a TEM microscope (FEI Tecnai TF20 TEM).

Results

FIG. 1 shows a schematic illustration of two approaches to isolating nanomaterials, as exemplified with isolation from *Poria cocos*.

Aqueous Boiling Method

Analysis of the supernatant by TEM revealed the existence of both spherical and rod-shaped particles. The existence of nanoparticles was further confirmed by SEM analysis of lyophilized powder.

Aqueous Boiling in the Presence of SPIO Nanodots

A magnet was used first to isolate compounds capable for forming supramolecular nanoparticles from an aqueous *Poria cocos* soup, by its magnetic force pulling on SPIO nanodots which were used as a model cargo to be encapsulated by supramolecular nanoparticles. Subsequently magnet was used to remove SPIO nanodots from the isolated supramolecular nanoparticles following dissolution of the latter in an appropriate organic solvent (here DCM), i.e., purifying the specific compounds in an organic solvent to remove SPIO nanodots. Resuspension of the purified compounds in water or an aqueous medium, processed through a boiling and cooling procedure, permitted the formation of supramolecular nanoparticles based on these specific compounds.

Following aqueous boiling with SPIO nanodots and cooling, supramolecular nanoparticles isolated from *Poria cocos* encapsulating SPIO nanodots was confirmed by TEM. SPIO nanodots-containing supramolecular nanoparticles obtained through the boiling/cooling procedures were able to dissolve in organic solvent dichloromethane (DCM), indicating the obtained nanomaterials (i.e., the specific compounds from *Poria cocos* capable of forming supramolecular nanoparticles) are hydrophobic or amphiphilic. Following removal of SPIO nanodots from the isolated compounds capable of forming supramolecular nanoparticles, TEM analysis confirmed resuspended purified compounds in water have particles, most of which were rod-shaped.

Chemical Extraction Method

To further simplify the process, a chemical extraction approach without the need for heating was employed. TEM analysis found that the obtained SPIO nanodots-encapsulated supramolecular nanoparticles had a morphology assimilar to those isolated through the aqueous boiling approach.

Thin-layer chromatography (TLC) analysis showed that the extracts from crude *Poria cocos* capable of forming supramolecular nanoparticles were similar between those isolated through the chemical extraction approach and those isolated through the aqueous boiling approach.

The *Poria cocos* extracts without SPIO nanodots were further separated using column chromatography (CC). Different fractions were evaluated for their abilities to form nanoparticles. Through these procedures, two compounds were obtained that form nanoparticles. $^1$H-NMR, $^{13}$C-NMR, and mass spectrometry analyses identified them as poricoic acid A (PAA) and dehydrotrametenolic acid (DTA). Both PAA and DTA formed nanorods ~400 nm long and with a diameter of ~100 nm.

Inclusion of polyvinyl alcohol (PVA), a surfactant used in nanoparticle synthesis, further improved the morphology of supramolecular nanoparticles and reduced aggregation. Therefore, PVA was included in nanoparticle preparation in the following examples.

Example 2. Identification and Isolation of Nanomaterials from Other Medicinal Natural Products (MNPs)

To identify functional nanomaterials from MNPs, chemical extraction approach was employed in the screening of 67 additional MNPs.

In total, five classes of nanomaterials were identified including:
(1) diterpene resin acids, such as abietic acid (AA) and pimaric acid (PA);
(2) phytosterols, such as stigmasterol (ST) and β-sitosterol (BT);
(3) lupane-type pentacyclic triterpenes, such as lupeol (LP) and betulinic acid (BA);
(4) oleanane type pentacyclic tritepenes, such as glycyrrhetic acid (GA) and sumaresinolic acid (SA);
(5) lanostane-type triterpenes and derivatives, such as dehydrotrametenolic acid (DTA) and poricoic acid A (PAA) in Example 1.

Table 1 summarizes properties of supramolecular nanoparticles formed from these compounds isolated from different medicinal natural products. Among them, LP, GA, SA, PA, and AA formed spherical supramolecular nanoparticles of diameters ranging from 130 nm to 218 nm; others formed nanorods with a diameter of ~100 nm and lengths of ~400 nm. All supramolecular nanoparticles exhibited negatively charged surfaces with a zeta potential ranging from −18.2 to −25.6 mV. All of them were capable of drug encapsulation with loading efficiency ranging from 33.7% to 68.3% using paclitaxel as a model drug. The input of paclitaxel to these compounds were 20% by weight, i.e., 20 mg paclitaxel in every 100 mg of a specific compound.

TABLE 1

Characterizations of supramolecular nanoparticles based on different isolated medicinal natural products.

| | Morphology | Average size (nm) | Zeta-potential (Mv) | Encapsulation efficiency (%) | Loading (% by wt) |
|---|---|---|---|---|---|
| Glycyrrhetic acid | Nanosphere | 218.2 | −25.2 | 68.3 | 18.5 |
| Sumaresinolic acid | Nanosphere | 156.3 | −19.2 | 33.7 | 10.2 |
| Lupeol | Nanosphere | 129.6 | −23.6 | 42.7 | 14.2 |
| Pimaric acid | Nanosphere | 197.2 | −25.4 | 48.3 | 13.6 |

TABLE 1-continued

Characterizations of supramolecular nanoparticles based on different isolated medicinal natural products.

|  | Morphology | Average size (nm) | Zeta-potential (Mv) | Encapsulation efficiency (%) | Loading (% by wt) |
|---|---|---|---|---|---|
| Abietic acid | Nanosphere | 137.4 | −25.6 | 49.7 | 12.3 |
| Betulinic acid | Nanorod | 64.3 × 373.7 | −19.9 | 47.3 | 15.7 |
| Dehydrotrametenolic acid | Nanorod | 101.3 × 423.5 | −20.1 | 49.7 | 14.4 |
| Poricoic acid A | Nanorod | 81.7 × 420.3 | −20.8 | 42.3 | 12.1 |
| β-Sitosterol | Nanorod | 98.6 × 496.7 | −24.9 | 50.4 | 15.2 |
| Stigmasterol | Nanorod | 132.1 × 479.2 | −18.2 | 48.3 | 12.1 |

Both *Artemisia annua* L and *Taxus* were found to contain BT capable of forming nanomaterials, which as a carrier was suitable for delivery of drug agents with low bioavailability such as artemisinin and paclitaxel. *Poria cocos* and *Radix Glycyrrhizae*, two most commonly used MNPs but often considered "redundant", were highly enriched with PA capable of forming nanomaterials.

Example 3. Enhanced Bioavailability of Agents Delivered Via Supramolecular Nanoparticles; and Toxicity Study of Supramolecular Nanoparticles Materials and Methods
Bioavailability of Delivered Agent
Rhodamine B-loaded supramolecular nanoparticles (SNPs) based on the identified compounds in Example 2 were prepared via the chemical extraction approach as described in Example 1. These SNPs were administered to mice via oral gavage. The oral bioavailability of SNPs was determined by quantifying the fluorescence of rhodamine B in the blood and calculated based on the area under the curve (AUC).

Toxicity of Supramolecular Nanoparticles
Toxicity of all the SNPs was evaluated using Caco-2 human intestinal cells. Caco-2 cells were purchased from American Type Culture Collection (ATCC, Rockville, Md., USA). Cells were grown in DMEM medium (Invitrogen) supplemented with 10% fetal bovine serum (FBS, Invitrogen), 100 units/mL penicillin, and 100 µg/mL streptomycin (Invitrogen) in a 37° C. incubator containing 5% $CO_2$.

Cells were plated in a 96-well plate. After overnight incubation, cells were treated with SNPs. After 72 hours, cell proliferation was quantified using the standard dimethyl thiazolyl diphenyl tetrazolium salt (MTT) assay. 10 mg/mL MTT in PBS was added to the cells resulting in a final MTT concentration of 1 mg/mL. The cells were incubated for an additional 4 hours at 37° C. Afterward, the media was removed, and 150 µL DMSO was added to each well to dissolve the formazan crystals. The absorption was measured at 570 nm using a BioTek Instrument ELx800 microplate reader. Each sample was prepared in triplicate. Data was reported as mean±SD. The percentage cell viability of each sample was determined relative to the control (untreated) cells.

Figure 2:
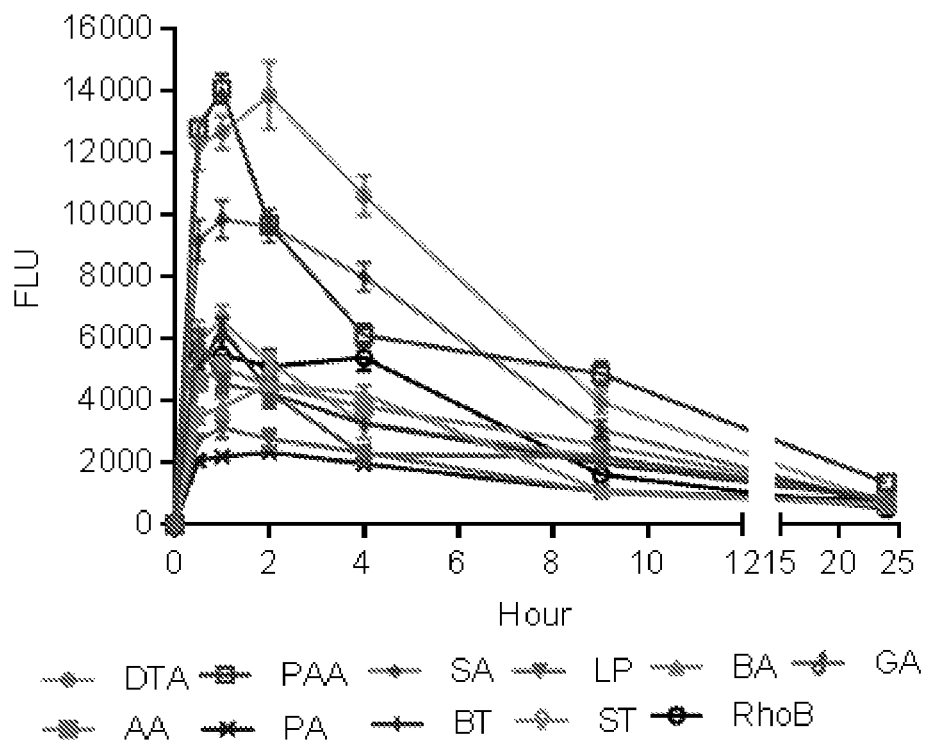
FIG. 2 is a line graph showing the mean plasma concentration of rhodamine as measured by fluorescent intensity (FLU) (arbitrary unit) over time (hour) following oral administration of different supramolecular nanoparticles formed from dehydrotrametenolic acid (DTA), poricoic acid A (PAA), sumaresinolic acid (SA), lupeol (LP), betulinic acid (BA), glycyrrhetic acid (GA), abietic acid (AA), pimaric acid (PA), β-sitosterol (BT), and stigmasterol (ST). These supramolecular nanoparticles encapsulated rhodamine B for quantification purposes. As a control, oral administration of rhodamine B (RhoB) was included.

Results
All SNPs (loaded with rhodamine B) demonstrated certain degrees of oral bioavailability. Among them, SNPs formed from DTA, PAA, and SA exhibited the highest oral delivery efficiency (FIG. 2). Free rhodamine B (RhoB) administered via oral gavage was used as a control.

Figure 3:
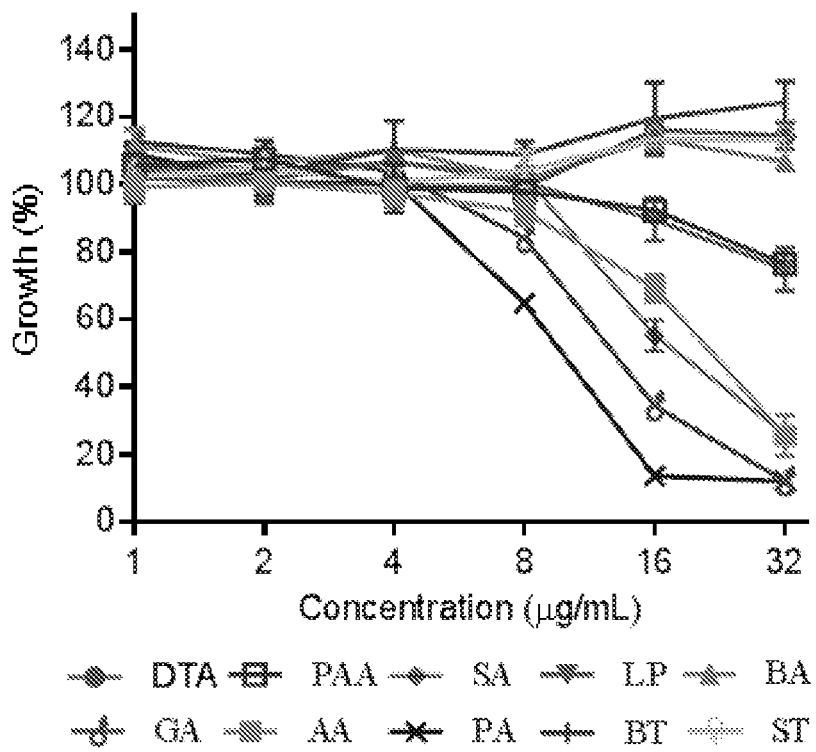
FIG. 3 is a line graph showing the percentage of growth (%) of Caco-2 human intestinal cells over different concentrations (μg/mL) of the identified compounds capable of forming supramolecular nanoparticles, including DTA, PAA, SA, LP, BA, GA, AA, PA, BT, and ST.

FIG. 3 shows all tested SNPs, except AA, SA, GA, and PA, exhibited favorable toxicity at the tested concentrations.

Dehydrotrametenolic acid (DTA) SNPs were selected for further characterizations due to the high oral bioavailability, efficient drug encapsulation, and favorable cytotoxicity.

Example 4. Uptake of Dehydrotrametenolic Acid (DTA) Supramolecular Nanoparticles (SNPs) by Intestine was Mediated Via Apical Sodium-Dependent Bile Transporter (1) Molecular Structural Basis for SNPs
The chemical structure of DTA SNPs were characterized using X-ray crystallography, X-ray diffraction (XRD), and 2-D Fourier transform infrared spectroscopy (FTIR) to study the molecular mechanisms of the formation of stable supramolecular nanoparticles.

Figure 18:
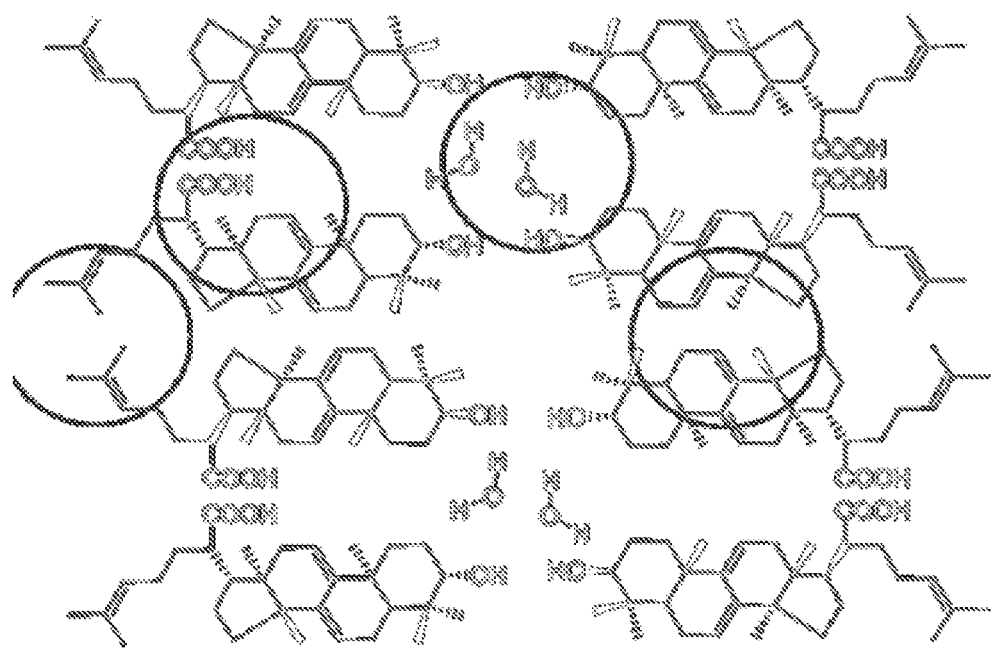
FIG. 18 is a schematic representation of the molecular organization of supramolecular nanoparticles formed by emulsifying dehydrotrametenolic acid (DTA SNPs), showing in the circles the intermolecular bondings as characterized via X-ray crystallography.

To determine the molecular forces that maintain the structure of DTA SNPs, the structure of a single crystal of DTA was analyzed by X-ray crystallography. Crystallographic analysis showed that the DTA molecule was nearly planar and interacted in a slipped-stack geometry directed by the intermolecular C=O . . . O—H hydrogen bonding, H—O . . . H—O—H hydrogen bonding, CH . . . π interaction, C=C . . . HC interaction and CH . . . HC interaction, as shown in FIG. 18.

Figure 19:
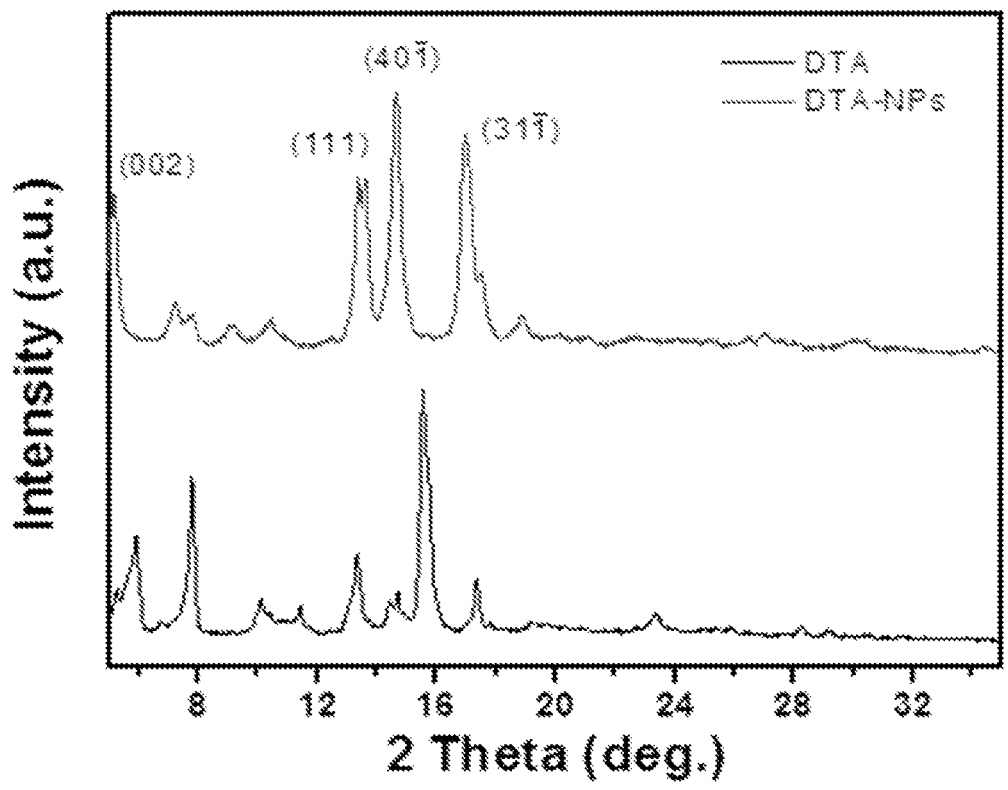
FIG. 19 is an X-ray diffraction spectrum comparing DTA molecules and DTA SNPs (denoted as DTA-NPs in the spectrum).

To reveal how DAT SNPs assembled, the X-ray diffraction (XRD) patterns of both bulk DTA and DTA SNPs were measured. FIG. 19 shows compared with the XRD pattern of bulk DTA, the XRD pattern of DTA SNPs displayed a significant increase in diffraction peak of (401), suggesting that DTA SNPs assemble preferentially along the [401(−)] direction.

DTA SNPs was also analyzed in two-dimensional infrared spectroscopy (2D-IR). Free DTA was used as a control. There were marked differences in the IR spectra between DTA SNPs and free DTA during thermal perturbation. The most dramatic changes were seen in the range of 1580-1760 $cm^{-1}$, where the C=O bond is assigned, and 3088-3704 $cm^{-1}$, where the O—H bond is assigned. The peaks for C=O bond, which were identified at 1703 $cm^{-1}$ and 1720 $cm^{-1}$ in the spectrum for free DTA, shifted to 1690 $cm^{-1}$ and 1701 $cm^{-1}$ in the spectrum for DTA SNPs, indicating that the carboxylic group in DTA is involved in DTA SNP structure formation. The peaks for O—H bond in the acid group of free DTA locate at 3432 $cm^{-1}$ and 3523 $cm^{-1}$ in the spectrum. By contrast, only one broad peak was seen in the spectrum for DTA SNPs 3387 $cm^{-1}$, indicating of the presence of hydrogen bonds among hydroxyl groups. Control analysis confirmed that the observed differences between DTA and DTA SNPs in the specific spectral region was not caused by, if any, residual surfactant PVA.

Molecular interaction analysis based on multiple spectra showed significant differences between DTA in the SNP form and DTA in its free form. Preliminary analysis indicated the structure of DTA SNPs was highly organized.

(2) Penetration Through GI Track

DTA SNPs encapsulating a near-infrared fluorescent dye, IR780, were prepared and administered to mice via oral gavage. After one hour, the GI tract was isolated, extensively washed, and imaged by IVIS®. Unlike free IR780 which located mostly in the stomach, the majority of IR780-containing DTA SNPs were located in the ileum. Further imaging by confocal microscopy identified a significant quantity of DTA SNPs inside the villi on the basolateral side of the epithelial cells. In contrast, mice that were orally administered with free rhodamine B, a fluorescent dye, had limited fluorescence.

These results showed that DTA SNPs survived the GI tract and crossed the intestinal epithelium. To confirm their stability in the GI environment, DTA SNPs were assayed via incubation in simulated gastric fluid (SGF, pH 1.2) and simulated intestinal fluid (SIF, pH 6.8) for 2 hours. SEM imaging showed the morphologies of DTA SNPs in phosphate buffered saline (PBS), in SGF, and in SIF were similar. This showed incubation in both SGF and SIF did not change the morphology of DTA SNPs, indicating DTA SNPs could survive in the harsh stomach environment.

(3) Mediated by Apical Sodium-Dependent Bile Transporter

Apical sodium-dependent bile transporter (ASBT) is highly expressed on the apical membrane of enterocytes and is responsible for the reabsorption of bile acids from the ileum. The ASBT system is highly efficient, accommodating the transport of ~20 g of bile acids daily (Stellaard F, et al., *J Lipid Res*, 25, 1313-1319 (1984); Kuipers F, et al., *Nat Rev Endocrinol*, 10, 488-498 (2014)).

ASBT was overexpressed in Caco-2 cells, as confirmed by flow cytometry analysis. Caco-2 cells with and without ASBT over-expression were individually treated with rhodamine B-loaded DTA SNPs. For flow cytometry analysis, stable ASBT-overexpressing Caco-2 cells and vector control cells were generated through lentiviral transduction in the preliminary study and treated with rhodamine B-loaded nanoparticles. After 4 hours of incubation, cells were harvested, fixed, and stained with anti-ASBT antibody (R&D Systems), and analyzed by flow cytometry.

Figure 4:
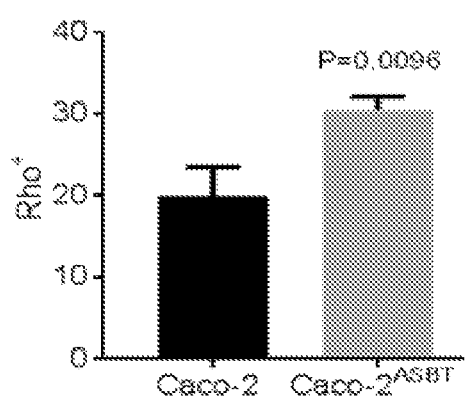
FIG. 4 is a bar graph showing the quantification of rhodamine B in Caco-2 cells, as well as in Caco-2 cells overexpressing apical sodium-dependent bile transporter (ABST), following treatment of these cells with rhodamine B-loaded dehydrotrametenolic acid-based supramolecular nanoparticles (DTA SNPs).

FIG. 4 shows overexpression of ASBT enhanced the uptake of DTA SNPs by Caco-2 cells by 52.8%.

Figure 5:
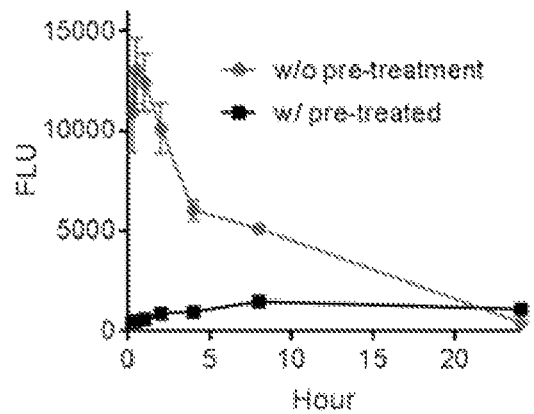
FIG. 5 is a line graph showing the uptake of DTA SNPs encapsulating rhodamine B as measured by plasma FLU (arbitrary unit) over time (hour) following oral administration to BALB/c mice without (w/o) or with (w/) pretreatment of 10 mg ursodeoxycholic acid, a natural substrate of ASBT.

FIG. 5 shows mice pretreated with ursodeoxycholic acid, a natural substrate of ASBT, prior to being administered with DTA SNPs effectively reduced the oral uptake of DTA SNPs. For this ligand competition study, mice received oral administration of 500 mg/kg of ursodeoxycholic acid. After 15 min, rhodamine B-loaded nanoparticles were administered. Control mice received nanoparticles without pretreatment. Taken together, these results showed the uptake of DTA SNPs in the small intestine was likely mediated by ASBT.

Example 5. Oral Delivery of Chemotherapeutics Via DTA SNPs Greatly Enhanced the Bioavailability of Oral Formulation of Chemotherapeutics Materials & Methods DTA SNPs for oral delivery of chemotherapy was evaluated using paclitaxel (PTX) as a model drug. PTX is a MNP-derived compound that has a low level of oral bioavailability of less than 2% (Beijnen J H, et al., *Semin Oncol* 21, 53-62 (1994); Choi J S, et al., *Int J Pharm* 280, 221-227 (2004)). PTX was encapsulated into DTA SNPs at an efficiency of 49.7%, for an input amount of PTX at 20% by weight of that DTA, resulting in PTX loaded at 14.4% by weight in DTA SNPs, as shown in Table 1.

Human breast adenocarcinoma cell line, MDA-MB-231 cells, were purchased from American Type Culture Collection (ATCC, Rockville, Md., USA). Cells were grown in DMEM medium (Invitrogen) supplemented with 10% fetal bovine serum (FBS, Invitrogen), 100 units/mL penicillin, and 100 g/mL streptomycin (Invitrogen) in a 37° C. incubator containing 5% $CO_2$.

In Vitro Drug Release

Drug-loaded supramolecular nanoparticles (3 mg) were suspended in 1 mL buffer and incubated at 37° C. with gentle shaking. At each sampling time, nanoparticles were centrifuged for 10 min at 12,000 rpm. The supernatant was collected for quantification of the encapsulated agent and 1 mL buffer was added for continued monitoring of release. The amounts of dye and non-fluorescent agents in supernatant were quantified based on fluorescence using a BioTek microplate reader and HPLC, respectively.

Results

SEM analysis confirmed encapsulation of PTX did not alter the morphology of DTA SNPs.

Figure 6:
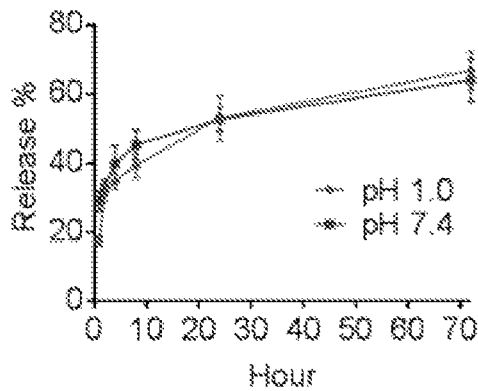
FIG. 6 is a line graph showing the cumulative release (%) over time (hour) of paclitaxel (PTX) from DTA SNPs incubated in a pH 7.4 medium and in a pH 1.0 medium.
Figure 7:
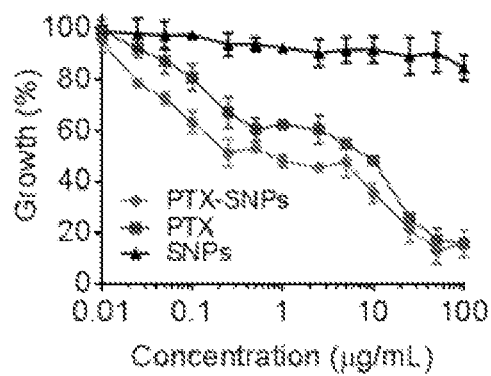
FIG. 7 is a line graph showing the percentage of growth (%) of human breast cancer MDA-MB-231 cells over different concentrations (μg/mL) of different samples: PTX, DTA SNPs (denoted in this graph as SNPs), PTX-encapsulated DTA SNPs (denoted as PTX-SNPs).

FIG. 6 shows exposure to pH 1.0 did not change the release of PTX from DTA SNPs. FIG. 7 shows PTX-loaded DTA SNPs and free PTX exhibited comparable toxicity on human breast cancer MDA-MB-231 cells in vitro.

Figure 8:
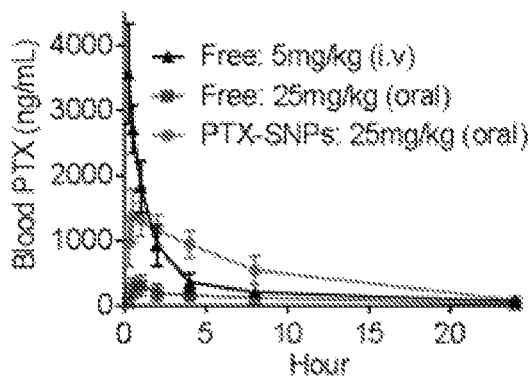
FIG. 8 is a line graph showing the mean plasma concentration of PTX (ng/mL) over time (hour) following administration of (1) free PTX at 5 mg/kg of animals via intravenous administration, (2) free PTX at 25 mg/kg of mice bearing MDA-MB-231 breast tumors via oral administration, or (3) PTX-encapsulated DTA SNPs (denoted as PTX-SNPs) containing 25 mg PTX/kg of animals via oral administration.

FIG. 8 shows encapsulation via DTA SNPs significantly enhanced the oral bioavailability of PTX. Oral administration of PTX-loaded DTA SNPs (PTX-SNPs) at 25 mg/kg of mouse resulted in an area-under-the curve (AUC) comparable to that of intravenous administered free PTX at 5 mg/kg of mouse in a mixture of Cremophor EL and ethanol.

Example 6. Preferential Accumulation of SNPs in Tumor and Delivery of Chemotherapeutics Via SNPs to Reduce Tumor Size (1) DTA SNPs: Intravenous administration Methods For this biodistribution study of supramolecular nanoparticles in tumors, female athymic (NCr-nu/nu) nude mice were used and maintained in a sterile environment. To establish tumors, mice received subcutaneous flank injections of $1\times10^6$ MDA-MB-231 tumor cells. Tumor size was measured weekly using traceable digital vernier calipers (Fisher). Tumor volume was determined by measuring the length (1) and width (w), and then calculating the volume (V) using the following formula: $V=lw^2/2$. Tumor homing study was started when the volume reaches ~200 $mm^3$ (day 1). Mice were randomly divided into two groups (n=5), which received intravenous treatment of IR780 or IR780-loaded nanoparticles (normalized based on fluorescence). 24 hours later, the mice were euthanized and the tumors were isolated and imaged.

Results

Figure 9:
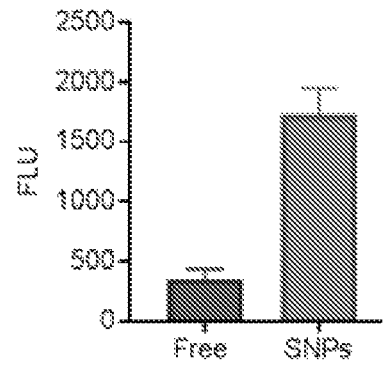
FIG. 9 is a bar graph showing the amount of IR780 as measured by FLU (arbitrary unit) in excised tumors from mice bearing MDA-MB-231 tumors that have been intravenously administered with IR780-loaded DTA SNPs or with free IR780.

FIG. 9 shows DTA SNPs significantly enhanced the accumulation of IR780 in tumors. Tumor tissues were extracted, and the amount of the IR-780 dye was quantified. The average concentration of IR780 in tumors in the animal group administered with DTA SNP was 4.9 times greater than that in the group administered with the free dye. The preferential accumulation in tumors of DTA SNPs was likely due to an enhanced permeability and retention (EPR) effect (Jain R K, et al., *Cancer Metastasis Rev* 6, 559-593 (1987)).

(2) DTA SNPs: Oral Administration

Methods

The therapeutic benefit of PTX-loaded DTX SNPs was evaluated for treatment of oral cancer. Mice bearing MDA-MB-231 tumors of ~50 mm$^3$ size were treated twice a week with orally injected saline (as a control), empty DTA SNPs, free PTX, or PTX-loaded DTX SNPs (denoted as PTX-SNPs). Tumor volumes were measured three times a week. Mice were euthanized when tumor volume reached ~1000 mm$^3$, at which point the tumors were excised and fixed in formalin for immunohistochemistry. Serial sections were obtained and stained with TUNEL for analysis of cellular apoptosis. The growth curve was plotted using the mean of the tumor volumes for each treatment group, at each time point.

Results

Figure 10:
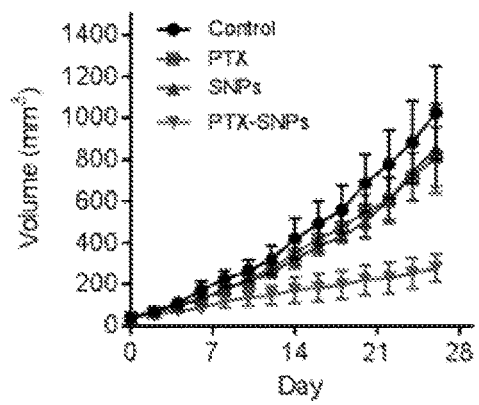
FIG. 10 is a line graph showing the size of tumor (volume in $mm^3$) in mice over time (day) following oral administration at twice a week with control saline (denoted control), empty DTA SNPs (denoted in this graph as SNPs), free PTX, or PTX-encapsulated DTA SNPs (denoted as PTX-SNPs).

FIG. 10 shows oral administration of PTX-SNPs reduced tumor volumes by 73% compared to the control group that received saline treatment. In contrast, treatments with free PTX or empty DTA SNPs reduced tumor volumes by only 21% and 17%, respectively. Oral administration of PTX-SNPs did not induce obvious toxicity, as no weight loss was observed in all treatment groups. Histologically, tumors from control treatments revealed a highly cellular mass with prominent nuclei; in contrast, tumors from animals treated with PTX-SNPs exhibited a much lower cellular mass, a lower nuclear-cytoplasmic ratio, and a marked increase in the number of apoptotic cells measured by TUNEL staining.

(3) OA SNPs: Intravenous Administration

Figure 11:
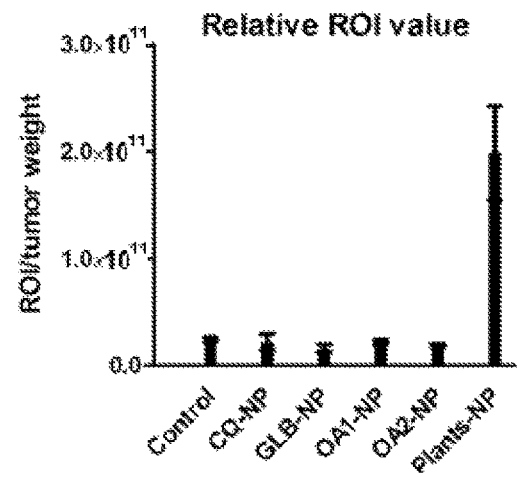
FIG. 11 is a bar graph showing the signal of IR780 per unit of tumor weight (ROI/tumor weight) in animals containing a MDA-MB-231 flank tumor model that have been intravenously administered with (1) saline (control), (2) poly(lactic-co-glycolic acid) (PLGA) nanoparticles loaded with, (3) PLGA nanoparticles conjugated with glyburide (denoted as GLB-NP), (4) PLGA nanoparticles conjugated with oleanolic acid (—COOH) (denoted as OA1-NP), (5) PLGA nanoparticles conjugated with oleanolic acid (—OH) (denoted as OA2-NP), or (6) oleanolic acid-based supramolecular nanoparticles (denoted as Plants-NP).

Oleanolic acid-based supramolecular nanoparticles were identified and prepared in a method as described in Examples 1 and 2, forming OA SNPs, also referred to as Plants-NP in FIG. 11. These nanoparticles were intravenously administered to animals with a MDA-MB-231 flank tumor model. For comparison, animals administered with saline (control), poly(lactic-co-glycolic acid) (PLGA) nanoparticles with CQ, PLGA nanoparticles conjugated with glyburide, PLGA nanoparticles conjugated with oleanolic acid (—COOH), and PLGA nanoparticles conjugated with oleanolic acid (—OH) were also examined.

FIG. 11 shows oleanolic acid-based supramolecular nanoparticles (OA SNPs, denoted as Plants-NP) had the highest signal, thus accumulation, in the tumor, as confirmed by imaging of tumor excised tissue from animals.

Next, drug delivery via encapsulation in OA SNPs was assayed in treating the flank tumor model.

Figure 12:
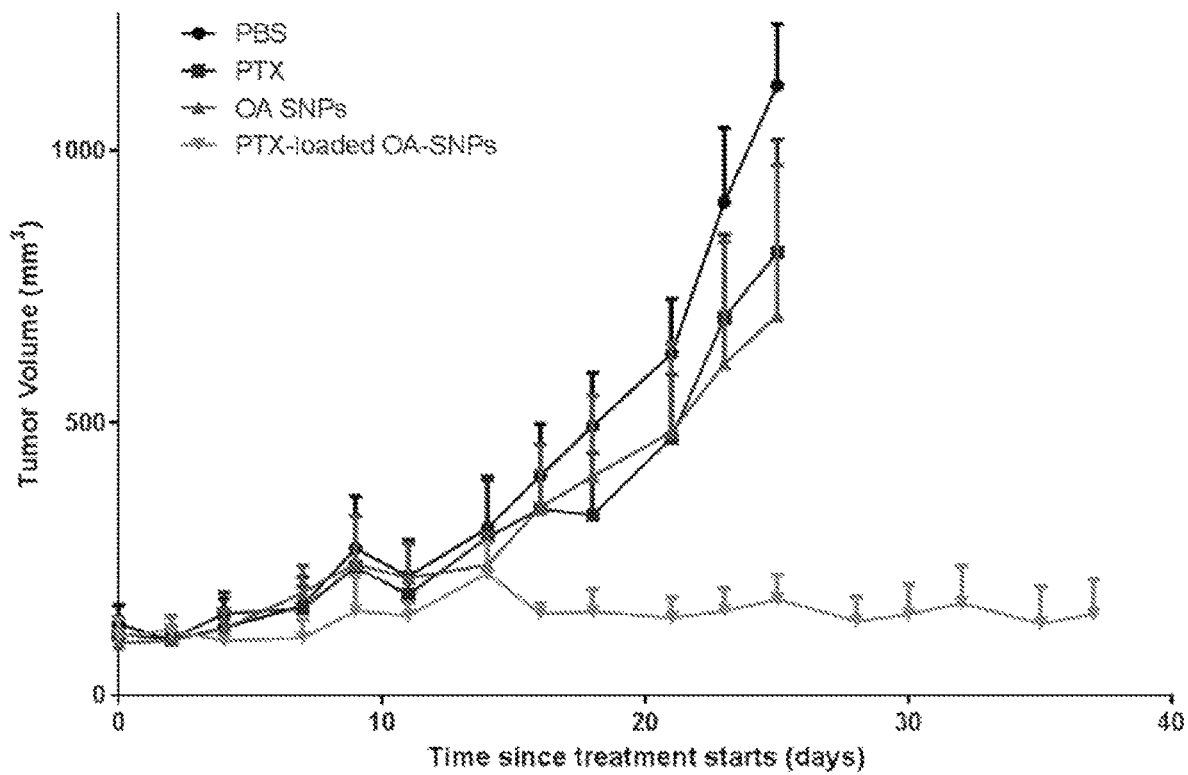
FIG. 12 is a line graph showing the size of tumor (volume in $mm^3$) over time (day) in animals bearing a MDA-MB-231 flank tumor model following intravenous administration of (1) phosphate buffered saline (PBS), (2) PTX, (3) oleanolic acid-based supramolecular nanoparticles (OA SNPs), or (4) PTX-loaded OA SNPs.

FIG. 12 shows animals intravenously administered with OA SNPs loaded with paclitaxel (PTX-loaded OA SNPs) had the smallest tumor volume over 30 days following treatment, which indicated the tumor did not grow following treatment. This is in contrast to animals intravenously administered with PBS, paclitaxel solution, or OA SNPs without paclitaxel, whose tumors grew substantially by 30 days following treatment.

Example 7. Oral Delivery of Glucagon-Like Peptide-1 (GLP-1) Via DTA SNPS

BACKGROUND

GLP-1 is a 30-aa peptide that is used in treating type 2 diabetes, due to its ability to control glucose and its beneficial effects on weight, blood pressure, β-cell survival, islet neogenesis, and cardioprotection (Koliaki C, et al., *Diabetes Ther* 2, 101-121 (2011); Nauck M A, et al., *Diabetologia* 36, 741-744 (1993)). However, translation of GLP-1 therapy is hindered by its short half-life (<2 min) in the circulatory system. Several long-acting, engineered GLP-1-based therapeutics have received FDA approval for clinical use, all of which are delivered by intravenous injection, which is associated with poor patient compliance. Long-acting GLP-1 formulations provide drug exposure for time periods exceeding the normal postprandial phase and thus induce significant side effects (Garber A J, et al, Am J Manag Care 16, S187-194 (2010)). Thus, it is preferred to administer GLP-1 orally at meal times to limit the exposure time.

Methods

For synthesis of GLP-1 (fragment 7-37)-loaded SNPs, a similar emulsion procedure to that in Example 1 was used, except that GLP-1(7-37) powder was dissolved in DMSO and added to the organic solvent immediately prior to emulsion.

Determining Efficacy of Glucose Regulation

Experiments were performed in balb/c (age 6-7 w) mice. 16 hours after fasting, mice received an i.p. injection of glucose at 4 g/kg, followed by oral delivery of GLP-1(7-37)-loaded SNPs. Blood samples were collected via tail snipping at 15 min, 30 min, 1 h, 2 h, 4 h, and 8 h time points. Serum glucose was determined using a One Touch glucose meter (Lifescan). Insulin was quantified using mouse/rat insulin ELISA kits (EMD Millipore). Mean plasma concentration of glucose or insulin—time curves were plotted. AUCs were calculated using MATLAB.

Statistical analysis All data were collected in triplicate and reported as mean and standard deviation. Comparison of two conditions was evaluated by the unpaired t-test. $p<0.05$ (*), 0.01 (), and 0.001 () were considered significant.

Results

GLP-1 (fragment 7-37) peptide was encapsulated into DTA SNPs. The resulting DTA SNPs, termed GLP-1-SNPs, contained 6.7% GLP-1 (7-37) by weight and possessed the same morphology as the DTX SNPs without encapsulation of a peptide.

Figure 13:
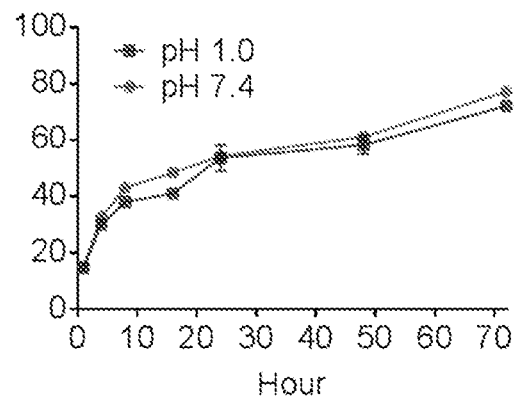
FIG. 13 is a line graph showing the cumulative release (%) over time (hour) of glucagon-like peptide-1 (GLP-1) from DTA SNPs when incubated in a pH 1.0 medium or a pH 7.4 medium.

FIG. 13 shows GLP-1-SNPs released in a medium of pH 7.4 over 70% of GLP-1 (7-37) over the course of three days in a controlled manner, and the release rate was not changed when the medium was at pH 1.0. This release characteristics was similar to the one of PTX-encapsulated DTX SNPs.

GLP-1-SNPs were evaluated in balb/c mice based on the intraperitoneal glucose tolerance test (IPGTT). 16 hours after fasting, mice received an intraperitoneal (i.p.) injection of glucose at 4 g/kg, followed by oral delivery of GLP-1-SNPs (3.0 mg GLP-1 equivalent/kg of mouse).

Figure 14:
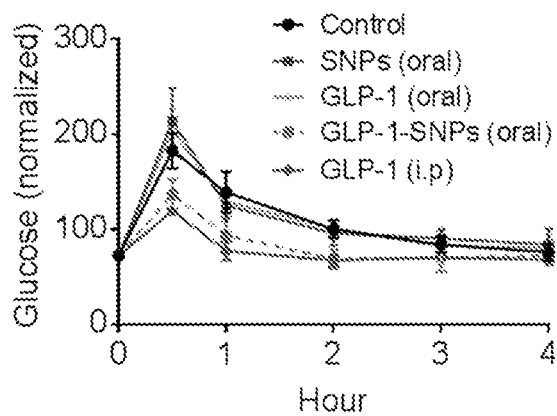
FIGS. 14 and 15 are line graphs showing the mean plasma concentration of glucose (normalized) (FIG. 14) and insulin (ng/mL) (FIG. 15), respectively, of balb/c mice over time (hour) in which the mice have previously been in 16 hours of fasting and received an intraperitoneal (i.p.) injection of glucose at 4 g/kg, followed by oral administration of (1) GLP-1-loaded DTA SNPs (at 3.0 mg of GLP-1 equivalent per kg of mouse), denoted as GLP-1-SNPs (oral); (2) GLP-1 delivered via i.p. injection; (3) GLP-1 delivered via oral administration; (4) DTA SNPs delivered via oral administration (denoted as SNPs (oral)); or (5) control, no treatment.

FIG. 14 shows oral delivery of GLP-1-SNPs decreased the glucose level in the blood by 22.6%, which was comparable to the level of reduction by i.p. injection of free GLP-1 at 33 µg/kg. In contrast, the control group administered with saline did not have significant decrease of glucose.

Figure 15:
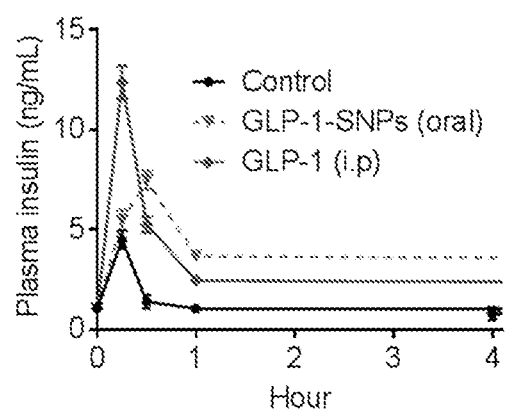

FIG. 15 shows the level of insulin increased with time after oral administration of GLP-1-SNPs. This was consistent with the change over time in blood glucose.

These results indicated DTA SNPs as a vehicle was able to deliver GLP-1 via oral administration for effective regulation on serum glucose.

DISCUSSION

These examples demonstrated the existence of functional nanomaterials in medicinal natural products. A group of small molecules were identified to be able to self-assemble into spherical or rod-shaped nanoparticles, termed supramolecular nanoparticles (SNPs). The resulting SNPs were capable of efficient drug encapsulation and penetration of the GI tract, therefore suitable for oral drug delivery of therapeutic, prophylactic, or diagnostic agents. Therefore, functional nanomaterials were shown to exist in and could be purified from medicinal natural products, which converted drug agents with poor bioavailability into a bioavailable form through the formation of SNPs that encapsulated or otherwise carried the drug agents.

The approach to identifying and collecting these functional nanomaterials (e.g., nanoparticles) is applicable to large-scale screening of medicinal natural products.

The SNPs from medicinal natural products show at least several advantages over conventional synthetic polymeric nanoparticles or lipid-based nanoparticles. These supramolecular nanoparticles are demonstrated to achieve targeted drug delivery and GI track barrier penetration without the need of additional chemical modifications. They are also stable in highly acidic environment, and are particularly suitable for use in oral delivery of therapeutic, prophylactic, or diagnostic agents.

One mechanism for SNPs to penetrate the GI track is by "hijacking" the ASBT-based bile acid transport system. This reveals a new avenue for enhancing oral drug delivery, unlike previous approaches of conjugating cargos or vehicles with targeting ligands specific for receptors expressed in intestinal epithelium such as vitamin B12 receptor and the neonatal Fc receptor (Chalasani K B, et al., *Journal of controlled release: official journal of the Controlled Release Society* 117, 421-429 (2007); Pridgen E M, et al., *Sci Transl Med,* 5, 213ra167 (2013)).

SNPs therefore efficiently mediate oral delivery of small molecule drugs and therapeutic peptides for effective disease treatment.

Example 8. Drug Delivery Via DTA SNPs to the Brain Following Intravenous Administration DTA SNPs were prepared to encapsulate an infrared dye, IR780, as in Example 6 and as described in Example 1. IR780-loaded DTA SNPs were tested in mice bearing GL261 gliomas. As a control, autocatalytic brain tumor-targeting poly(amine-co-ester) terpolymer nanoparticles (ABTT NPs) were prepared as described in PCT Patent Application no. PCT/US2016/027133.

Figure 16:
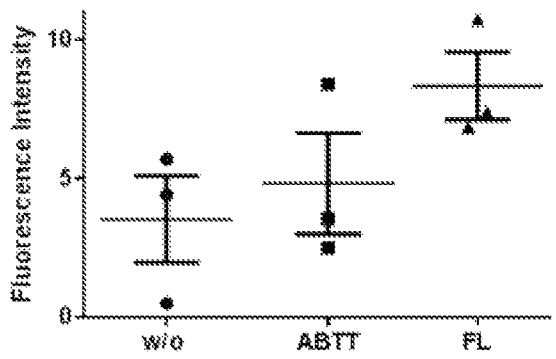
FIG. 16 is a dot graph showing the IR780 (near infrared fluorescence) intensity in tumor in the brain of mice bearing GL261 gliomas that have been intravenously administered with (1) PLGA nanoparticles without modification; (2) PLGA NPs engineered based on the autocatalytic brain tumor-targeting (ABTT) mechanism; or (3) DTA SNPs.

Intravenous administration of DTA SNPs resulted efficient penetration to the brain with brain tumors, stroke, or Alzheimer's disease. FIG. 16 shows DTA SNPs had the highest fluorescence signal in tumors in the brain, compared to ABTT nanoparticles and PLGA nanoparticles without modification (w/o), following intravenous administration.

Example 9. Oral Delivery of Glyburide Via DTA SNPs for Stroke Treatment

DTA SNPs were prepared to encapsulate glyburide. "Empty" DTA SNPs without encapsulating a drug agent were prepared as control. Free glyburide and saline were also control.

Animal model of stroke was middle cerebral artery occlusion (MCAO) performed in mice and rats.

Figure 17:
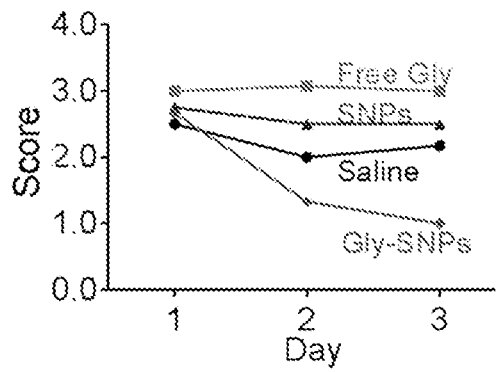
FIG. 17 is a line graph showing the score of neurological damage by middle cerebral artery occlusion (MCAO)-induced stroke in mice over time (days) following oral administration of (1) free glyburide; (2) DTA SNPs (denoted SNPs); (3) saline; or (4) glyburide-loaded DTA SNPs (denoted as Gly-SNPs).

FIG. 17 shows oral administration of glyburide-loaded DTA SNPs effectively improved the neurological scores. Glyburide-loaded DTA SNPs also reduced the infra volume in stroke mice and rats, as confirmed by imaging of brain tissue as labeled with 2,3,5 triphenyltetrazolium chloride (TTC Stain) or IR780.

We claim:

1. A supramolecular particle which is orally bioavailable comprising compounds selected from the group consisting of dehydrotrametenolic acid, sumaresinolic acid, dehydroabietic acid, lupeol, and poricoic acid A, having an average diameter between about 5 nm and 300 nm, wherein the particle penetrates the gastrointestinal tract.

2. The particle of claim 1, wherein the particle is in the form of a nanosphere, nanorod, or a combination thereof.

3. The particle of claim 1, wherein the particle is stable at the pH of the stomach.

4. The particle of claim 2, wherein the nanosphere has an average diameter between about 10 nm and 300 nm, and the nanorod has an average length between about 50 nm and 700 nm and an average width between about 5 nm and 150 nm.

5. Supramolecular particles comprising compounds selected from the group consisting of dehydrotrametenolic acid, sumaresinolic acid, betulinic acid, dehydroabietic acid, lupeol, poricoic acid A, and ursolic acid and a superparamagnetic nanodot.

6. The particle of claim 1 wherein the compounds are prepared by
heating plant or plant extract in an aqueous medium in the presence of superparamagnetic nanoparticles,
cooling the mixture to between about 3° C. and about 4° C.,
applying a magnetic force to isolated superparamagnetic nanoparticles and substances associated therewith, and
separating the substances from the isolated superparamagnetic nanoparticles to produce the compounds.

7. The particle of claim 6, wherein the superparamagnetic nanoparticles comprise superparamagnetic iron oxide with an average diameter of between about 2 nm and about 200 nm coated with oleic acid.

8. A method of preparing the supramolecular particle of claim 1 or claim 5 comprising emulsification, optionally in the presence of a surfactant, of the superparamagnetic nanoparticles and substances associated therewith.

9. A method of administering one or more therapeutic, prophylactic, nutraceutical and/or diagnostic agent to a subject comprising administering the supramolecular particle of claim 1 or claim 5 to a subject in need thereof.

10. The method of claim 9 comprising administering orally, intranasally, via inhalation, rectally, intravaginally, intrathecally, or via injection.

11. The method of claim 9 for treating symptoms of one or more neurological diseases or disorders.

12. The method of claim 9 for treating symptoms of a cancer or tumor.

13. The method of claim 9 for treating symptoms of a metabolic disorder such as diabetes.

14. The method of claim 9 for treating symptoms of an ischemic injury such as stroke.

15. A dosage unit of the supramolecular particle of claim 1 or claim 5 in the form of powder, a tablet, a capsule, a chewing gum, a suspension, or reconstitutable vial, optionally contains a pharmaceutically acceptable excipient.

16. The particle of claim 5, furthering comprising a therapeutic, prophylactic, nutraceutical or diagnostic agent, wherein the therapeutic, prophylactic, nutraceutical or diagnostic agent is encapsulated in, non-covalently associated with, or covalently bonded with the particle.

17. The particle of claim 16, wherein a therapeutic, prophylactic, or diagnostic agent is encapsulated in the particle at between about 0.5% and about 50%, by weight.

* * * * *

UNITED STATES PATENT AND TRADEMARK OFFICE
CERTIFICATE OF CORRECTION

PATENT NO. : 11,478,433 B2
APPLICATION NO. : 16/624803
DATED : October 25, 2022
INVENTOR(S) : Jiangbing Zhou, Xin Yang and Chao Ma Page 1 of 1

It is certified that error appears in the above-identified patent and that said Letters Patent is hereby corrected as shown below:

In the Claims

Claim 15, Column 54, Lines 55-56, replace "optionally contains a" with --optionally containing a--.

Signed and Sealed this
Twenty-sixth Day of September, 2023

Katherine Kelly Vidal
*Director of the United States Patent and Trademark Office*